(12) United States Patent
McGrath et al.

(10) Patent No.: US 9,925,310 B2
(45) Date of Patent: *Mar. 27, 2018

(54) BIOCOMPATIBLE AND BIOABSORBABLE DERIVATIZED CHITOSAN COMPOSITIONS

(71) Applicant: Tricol Biomedical, Inc., Portland, OR (US)

(72) Inventors: Barbara McGrath, Portland, OR (US); Simon McCarthy, Portland, OR (US); Sam Kuhn, Portland, OR (US); Alysha Wold, Portland, OR (US); Michael Stolten, Portland, OR (US); Amanda Bennett, Portland, OR (US)

(73) Assignee: Tricol Biomedical, Inc., Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/371,010

(22) Filed: Dec. 6, 2016

(65) Prior Publication Data

US 2017/0119934 A1    May 4, 2017

Related U.S. Application Data

(63) Continuation of application No. 14/211,632, filed on Mar. 14, 2014, now Pat. No. 9,547,011.

(60) Provisional application No. 61/784,467, filed on Mar. 14, 2013.

(51) Int. Cl.
| | | |
|---|---|---|
| *A61L 27/58* | (2006.01) | |
| *A61L 27/26* | (2006.01) | |
| *C08L 89/06* | (2006.01) | |
| *C08L 5/08* | (2006.01) | |
| *C08B 37/08* | (2006.01) | |
| *G01N 33/50* | (2006.01) | |

(52) U.S. Cl.
CPC .............. *A61L 27/58* (2013.01); *A61L 27/26* (2013.01); *C08B 37/003* (2013.01); *C08L 5/08* (2013.01); *C08L 89/06* (2013.01); *G01N 33/5014* (2013.01); *A61L 2400/04* (2013.01); *C08L 2201/06* (2013.01); *G01N 2333/545* (2013.01); *G01N 2400/28* (2013.01)

(58) Field of Classification Search
CPC .. A61K 9/0024; A61K 47/36; A61K 49/0008; A61L 27/20; A61L 27/26; C08B 37/0083; C08L 5/08
USPC ...... 514/23, 55, 77; 536/20, 55.3; 106/135.1
See application file for complete search history.

(56) References Cited

U.S. PATENT DOCUMENTS

| | | | |
|---|---|---|---|
| 4,532,134 A | 7/1985 | Malette et al. | |
| 4,803,078 A | 2/1989 | Sakai | |
| 4,960,413 A | 10/1990 | Sagar et al. | |
| 5,166,187 A | * 11/1992 | Collombel | A61L 27/26 424/423 |
| 5,752,974 A | 5/1998 | Rhee et al. | |
| 5,885,609 A | 3/1999 | Amiji | |
| 5,894,070 A | 4/1999 | Hansson et al. | |
| 5,900,408 A | 5/1999 | Block et al. | |
| 6,448,462 B2 | 9/2002 | Groitzsch et al. | |
| 6,486,140 B2 | 11/2002 | Hansson et al. | |
| 6,521,243 B2 | 2/2003 | Hassan | |
| 6,858,222 B2 | 2/2005 | Nelson et al. | |
| 6,864,245 B2 | 3/2005 | Vournakis et al. | |
| 6,897,348 B2 | 5/2005 | Malik | |
| 6,967,261 B1 | 11/2005 | Soerens et al. | |
| 7,041,868 B2 | 5/2006 | Greene et al. | |
| 7,098,194 B2 | 8/2006 | Chenite et al. | |
| 7,125,968 B2 | 10/2006 | Yura et al. | |
| 7,141,714 B2 | 11/2006 | Nielsen | |
| 7,195,675 B2 | 3/2007 | Okazaki et al. | |
| 7,556,946 B2 | 7/2009 | Versali et al. | |
| 7,776,840 B2 | 8/2010 | Bitterman et al. | |
| 7,780,873 B2 | 8/2010 | Mora-Gutierrez et al. | |
| 7,820,872 B2 | 10/2010 | Gregory et al. | |
| 7,968,110 B2 | 6/2011 | Hubbard | |

(Continued)

FOREIGN PATENT DOCUMENTS

| | | | |
|---|---|---|---|
| CN | 1157568 A | 8/1997 | |
| CN | 1157569 A | 8/1997 | |

(Continued)

OTHER PUBLICATIONS

Sakai et al, Polymer Journal, 2001, 33(8), 640-42.*

(Continued)

*Primary Examiner* — Ganapathy Krishnan
(74) *Attorney, Agent, or Firm* — Seed IP Law Group LLP; Chandra E. Eidt

(57) ABSTRACT

The invention relates to biocompatible, bioabsorbable derivatized non-crosslinked chitosan compositions optionally crosslinked to gelatin/collagen by 1-ethyl-3-[3-dimethylaminopropyl] carbodiimide hydrochloride (EDC) for biomedical use and methods of making and testing such compositions, including a modified acute systemic toxicity test. The compositions comprise derivatized chitosan reacetylated to a degree of N-deacetylation (DDA) of between about 15% and 40%. The compositions are typically bioabsorbed in about 90 days or less and can be made to bioabsorb at differing rates of speed. The compositions are initially soluble in aqueous solution below pH 6.5. The compositions have an acid content that can be adjusted between about 0% (w/w) and about 8% (w/w) to customize the composition for uses that require and/or tolerate differing levels of cytotoxicity, adhesion, composition cohesion, and cell infiltration into the composition.

20 Claims, 16 Drawing Sheets

(56) References Cited

U.S. PATENT DOCUMENTS

| | | | |
|---|---|---|---|
| 8,012,907 B2 | 9/2011 | Berrada | |
| 8,119,780 B2 | 2/2012 | Baker et al. | |
| 8,303,980 B2 | 11/2012 | Hirose et al. | |
| 8,414,925 B2 | 4/2013 | Freier | |
| 8,513,217 B2 | 8/2013 | Chen et al. | |
| 8,691,882 B2 | 4/2014 | Lee et al. | |
| 8,703,924 B2 | 4/2014 | Andersson | |
| 8,932,983 B1 | 1/2015 | Harris et al. | |
| 9,192,574 B2 | 11/2015 | Medina et al. | |
| 9,547,011 B2* | 1/2017 | McGrath | A61L 27/20 |
| 2004/0047892 A1 | 3/2004 | Desrosiers et al. | |
| 2005/0118238 A1 | 6/2005 | Zhu et al. | |
| 2005/0123588 A1 | 6/2005 | Zhu et al. | |
| 2005/0181027 A1 | 8/2005 | Messinger | |
| 2005/0226905 A1 | 10/2005 | Tien et al. | |
| 2005/0240137 A1 | 10/2005 | Zhu et al. | |
| 2007/0104769 A1 | 5/2007 | Feng et al. | |
| 2007/0148215 A1 | 6/2007 | Teslenko et al. | |
| 2007/0202142 A1 | 8/2007 | Laugier et al. | |
| 2008/0200948 A1 | 8/2008 | Utecht et al. | |
| 2008/0248508 A1 | 10/2008 | Baker et al. | |
| 2009/0004230 A1 | 1/2009 | Chuetz et al. | |
| 2009/0022770 A1 | 1/2009 | Andersson | |
| 2009/0035356 A1 | 2/2009 | Bui-Khac et al. | |
| 2009/0148486 A1* | 6/2009 | Lu | A61K 9/0063 424/422 |
| 2010/0113618 A1* | 5/2010 | Berger | C08J 3/075 514/777 |
| 2010/0160467 A1* | 6/2010 | Lee | A61L 27/46 521/50 |
| 2010/0222297 A1 | 9/2010 | Teissedre et al. | |
| 2010/0260845 A1 | 10/2010 | Jayakrishnan et al. | |
| 2010/0316715 A1 | 12/2010 | Andersson | |
| 2011/0014279 A1 | 1/2011 | Mora-Gutierrez et al. | |
| 2011/0311632 A1 | 12/2011 | Roorda et al. | |
| 2016/0266143 A1 | 9/2016 | McGrath et al. | |

FOREIGN PATENT DOCUMENTS

| | | |
|---|---|---|
| FR | 2 736 835 A1 | 1/1997 |
| WO | 91/09163 A1 | 6/1991 |
| WO | 94/06484 A1 | 3/1994 |
| WO | 2005/024101 A1 | 3/2005 |
| WO | 2006/108364 A1 | 10/2006 |
| WO | 2006/131081 a1 | 12/2006 |
| WO | 2007/054039 A1 | 5/2007 |
| WO | 2008/000198 A2 | 1/2008 |
| WO | 2008/011840 A2 | 1/2008 |
| WO | 2008/028428 A1 | 3/2008 |
| WO | 2008/098526 A2 | 8/2008 |
| WO | 2008/106903 A2 | 9/2008 |
| WO | 2008/106904 A1 | 9/2008 |
| WO | 2008/137530 A1 | 11/2008 |
| WO | 2009/031047 A2 | 3/2009 |

OTHER PUBLICATIONS

Association for the Advancement of Medical Instrumentation, "Biological evaluation of medical devices—Part 13: Identification and quantification of degradation products from polymeric devices," ANSI/AAMI/ISO 10993-13, 1999, 17 pages.
ASTM International, "Standard Guide for Characterization and Testing of Biomaterial Scaffolds Used in Tissue-Engineered Medical Products," F2150-07, 2007. (10 pages).
ASTM International, "Standard Method for in vitro Degradation Testing of Hydrolytically Degradable Polymer Resins and Fabricated Forms for Surgical Implants," F1635-11, 2011. (7 pages).
ASTM International, "Standard Practice for Assessment of Compatibility of Absorbable/Resorbable Biomaterials for Implant Applications," F1983-99 (Reapproved 2008), 1999. (5 pages).
Baek et al., "Effects of Chitosan on Serum Cytokine Levels in Elderly Subjects," *Archives of Pharmacal Research* 30(12):1550-1557, 2007.

Baldrick, "The safety of chitosan as a pharmaceutical excipient," *Regulatory Toxicology and Pharmacology* 56(3):290-299, 2010.
Baxter et al., "Improved method for i.r. determination of the degree of N-acetylation of chitosan,", *International Journal of Biological Macromolecules* 14(3):166-169, 1992.
Berger et al., "Pseudo-thermosetting chitosan hydrogels for biomedical application," *International Journal of Pharmaceutics* 288(2):197-206, 2005.
Bueter et al., "Chitosan but not Chitin Activates the Inflammasome by a Mechanism Dependent upon Phagocytosis," *The Journal of Biological Chemistry* 286(41):35447-35455, 2011. (10 pages).
Freier et al., "Controlling cell adhesion and degradation of chitosan films by N-acetylation," *Biomaterials* 26(29):5872-5878, 2005.
Hein et al., "Selection of a Practical Assay of the Determination of the Entire Range of Acetyl Content in Chitin and Chitosan: UV Spectrophotometry With Phosphoric Acid as Solvent," *Journal of Biomedical Materials Research Part B: Applied Biomaterials* 86B(2):558-568, 2008.
Hirano et al., "A facile N-acylation of chitosan with carboxylic anhydrides in acidic solutions," *Carbohydrate Research* 41(1):C1-C2, 1975.
Hirano et al., "Selective N-acylation of chitosan," *Carbohydrate Research* 47(2):315-320, 1976.
Iso, "Biological evaluation of medical devices—Part 9: Framework for identification and quantification of potential degradation products," International Standard 10993-9, Dec. 15, 2009, 16 pages.
Jia et al., "Synthesis and antibacterial activities of quaternary ammonium salt of chitosan," *Carbohydrate Research* 333(1):1-6, 2001.
Kean et al., "Biodegradation, biodistribution and toxicity of chitosan," *Advanced Drug Delivery Reviews* 62(1):3-11, 2010.
Kim et al., "Chitosan implants in the rat spinal cord: Biocompatibility and biodegradation," *Journal of Biomedical Materials Research A* 97A(4):395-404, 2011.
Kofuji et al., "Relationship between physicochemical characteristics and functional properties of chitosan," *European Polymer Journal* 41(11):2784-2791, 2005.
Kurita et al., "Studies on Chitin, 3—Preparation of Pure Chitin, Poly(N-acetyl-D-glucosamine), from the Water-Soluble Chitin," *Die Makromolekulare Chemie* 178(9):2595-2602, 1977.
Lavertu et al., "Kinetics and efficiency of chitosan reacetylation," *Carbohydrate Polymers* 87(2):1192-1198, 2011.
Methacanon et al., "Heterogeneous N-deacetylation of squid chitin in alkaline solution," *Carbohydrate Polymers* 52(2):119-123, 2003.
Miya et al., "I.r. spectroscopic determination of CONH content in highly deacylated chitosan," *International Journal of Biological Macromolecules* 2(5):323-324, 1980.
Qun et al., "Effect of Reacetylation and Degradation on the Chemical and Crystal Structures of Chitosan," *Journal of Applied Polymer Science* 104(4):2720-2728, 2007.
Ren et al., "The enzymatic degradation and swelling properties of chitosan matrices with different degrees of N-acetylation," *Carbohydrate Research* 340(15):2403-2410, 2005.
Roberts, Chitin Chemistry, The MacMillan Press, Ltd., London, United Kingdom, 1992, pp. 86-91. (5 pages).
Sakai et al., "A Novel Method of Dissolving Chitosan in Water for Industrial Application," *Polymer Journal* 33(8):640-642, 2001.
Sannan et al, "Studies on Chitin, 2: Effect of Deacetylation on Solubility," *Die Makromolekulare Chemie* 177(12):3589-3600, 1976.
Sorlier et al., "Light Scattering Studies of the Solution Properties of Chitosans of Varying Degrees of Acetylation," *Biomacromolecules* 4(4):1034-1040, 2003.
Tomihata et al., "In vitro and in vivo degradation of films of chitin and its deacetylated derivatives," *Biomaterials* 18(7):567-575, 1997.
Tseng et al., "Characterization of chitosan-gelatin scaffolds for dermal tissue engineering," *Journal of Tissue Engineering and Regenerative Medicine* 7(1):20-31, 2011.
Vårum et al., "In vitro degradation rates of partially N-acetylated chitosans in human serum," *Carbohydrate Research* 299(1-2):99-101, 1997.

(56) References Cited

OTHER PUBLICATIONS

Xu et al., "Chitosan Film Acylation and Effects on Biodegradability," *Macromolecules* 29(10):3436-3440, 1996.
Yang et al., "The controlling biodegradation of chitosan fibers by N-acetylation in vitro and in vivo," *Journal of Materials Science: Materials in Medicine* 18(11):2117-2121, 2007.
Adali et al., "Synthesis, characterization and biocompatibility studies on chitosan-graft-poly(EGDMA)," *Carbohydrate Polymers* 77(1):136-141, 2009.
Bajaj et al., "Zwitterionic Chitosan Derivative, a New Biocompatible Pharmaceutical Excipient, Prevents Endotoxin-Mediated Cytokine Release," *PLoS One* 7(1):e30899, 2012. (10 pages).
Iso, "Biological evaluation of medical devices—Part 11: Tests for systemic toxicity," International Standard 10993-11, Aug. 15, 2006, 36 pages.
Medline, Accession No. NLM9513255, Misterka et al., "Changes in the level of interleukin-1 beta and interleukin-6 after implantation of selected medical materials: Introductory report," *Polimery W Medycynie* 28(1-2):15-24, 1998. (2 pages).

* cited by examiner

FIGURE 8C    FIGURE 8D
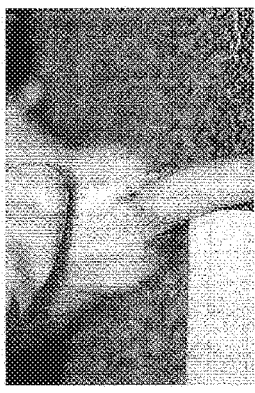
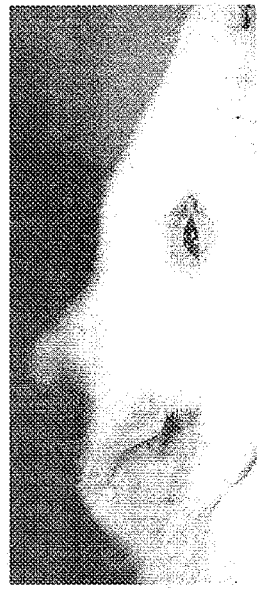
FIGURE 8A    FIGURE 8B Table of Material Compositions and Key Alpha Identifier Index

| Alpha ID | Condition | Evaluation | | | Biomaterial Composition and Characteristics | | | | | |
|---|---|---|---|---|---|---|---|---|---|---|
| | | Bio-material Source | Rat, IP implant | MLT | in vivo efficacy | [chitosan] | [gelatin] | [Acid] | [moisture] | other |
| A | 63% DDA chitosan + gelatin crosslink | | ✓ | | | 47% | 47% | ~1% | 5% | EDC: ~4% |
| B | 63% DDA chitosan + gelatin NOT crosslinked | | ✓ | | | 47% | 47% | ~1% | 5% | 0% |
| C | 63% DDA chitosan | | ✓ | ✓ | ✓ | 90% | 0% | 3.5% | ~6% | 0% |
| D | 63% DDA chitosan + lysozyme | 1a | | ✓ | ✓ | 90% | 0% | 3.5% | ~6% | lysozyme: |
| E | 88% DDA chitosan + gelatin | 2 | ✓ | | | 68% | 23% | 5% | 5% | 0% |
| F | 63% DDA chitosan + gelatin + lactic | | ✓ | | | 60% | 20% | ~15% Lactic | 5% | 0% |
| G | 63% DDA chitosan + gelatin | 1a | ✓ | | | 68% | 23% | 5.9% | 4% | 0% |
| H | 63% DDA chitosan, washed | | ✓ | | | 90% | 0% | 4.5% | 5% | 0% |
| I | mdoc + 63% DDA chitosan | 1b | ✓ | | | 71% | 0% | 0.5% | 5% | mdoc: 24% |
| J | 71% DDA chitosan + gelatin | 1a | ✓ | | | 68% | 23% | 5.5% | 4% | 0% |
| K | ~30% DDA | | | ✓ | | 93% | 0% | 1.9% | 5% | 0% |
| L | ~30% DDA w/ lysozyme | | | ✓ | | 93% | 0% | 1.9% | 5% | lysozyme: |
| M | chitosan to chitin (~0% DDA) in sponge form | | ✓ | | | 95% | 0% | 0% | 5% | 0% |
| N | 88% DDA chitosan | | | ✓ | | 93% | 0% | 1.9% | 5% | 0% |
| O | 65% DDA chitosan | 3 | | ✓ | | 93% | 0% | 1.9% | 5% | 0% |
| P | w/ lysozyme | | | ✓ | | | | | | lysozyme: |
| Q | 60% DDA chitosan | | | ✓ | | 93% | 0% | 1.9% | 5% | 0% |
| R | w/ lysozyme | | | ✓ | | | | | | lysozyme: |

Figure 9A.

| | Biomaterial Composition and Characteristics | | | | | | | |
|---|---|---|---|---|---|---|---|---|
| Alpha ID | Molecular weight- Mw (daltons) | Molecular weight- Mn (daltons) | DDA, FT-IR | DDA, NMR | DDA, PUV | Dimensions implanted (l x w x h) | Compression Thickness (mm) | Density (g/cc) |
| A | n/a | n/a | n/a | 63% | n/a | 10mm x 5mm x 5mm | 10mm- not compressed; 5mg (?)- cut in 1/2 | 0.02 |
| B | n/a | n/a | n/a | 63% | n/a | n/a | n/a | n/a |
| C | n/a | 41,625 | n/a | 63% | n/a | 10mm x 5mm x 1mm | 1mm; 14mg | 0.28 |
| D | 34,980 | 22,417 | n/a | 63% | n/a | 2040 mg/kg | n/a | n/a |
| E | n/a | 54,544 | n/a | 88% | n/a | 10mm x 5mm x 1mm | 1mm; 14mg | 0.28 |
| F | n/a | 69,957 | n/a | 63% | n/a | 10mm x 5mm x 1mm | 1mm; 14mg | 0.28 |
| G | 113,075 | 66,332 | n/a | 63% | n/a | 10mm x 5mm x 1mm | 1mm; 14mg | 0.28 |
| H | 78,485 | 37,209 | n/a | 63% | n/a | 10mm x 5mm x 1.5mm | 1.5mm; 14mg | 0.19 |
| I | n/a | n/a | n/a | 63% | n/a | 10mm x 5mm x 1.5mm | 1.5mm; 14mg | 0.19 |
| J | 104,295 | 69,698 | n/a | 71% | n/a | 10mm x 5mm x 1.5mm | 1.5mm; 14mg | 0.19 |
| K | 79,118 | 52,890 | n/a | n/a | 32% | 10mm x 5mm x 2mm | 2mm; 14mg | 0.14 |
| L | 47,991 | 39,807 | n/a | n/a | 32% | 2040 mg/kg | n/a | n/a |
| M | n/a | n/a | n/a | n/a | 19% | 10mm x 5mm x 8mm | 8mm; 14mg | 0.04 |
| N | 135,850 | 58,182 | 83% | 88% | 92% | 2000 mg/kg | n/a | n/a |
| O | 116,150 | 68,137 | 67% | n/a | n/a | 2000 mg/kg | n/a | n/a |
| P | 35,520 | 26,505 | n/a | n/a | n/a | 2040 mg/kg | n/a | n/a |
| Q | 113,230 | 55,026 | 59% | n/a | n/a | 2000 mg/kg | n/a | n/a |
| R | 35,710 | 26,431 | n/a | n/a | n/a | 2040 mg/kg | n/a | n/a |

Figure 9B.

| Alpha ID | Condition | Bio-material Source | Evaluation | | | Biomaterial Composition and Characteristics | | | | |
|---|---|---|---|---|---|---|---|---|---|---|
| | | | Rat, IP Implant | MLT | in vivo efficacy | [chitosan] | [gelatin] | [Acid] | [moisture] | other |
| S | 45% DDA chitosan | | | ✓ | | 93% | 0% | 1.9% | 5% | 0% |
| T | w/ lysozyme | | | ✓ | | | | | | lysozyme: |
| U | 35% DDA chitosan | | | ✓ | | 93% | 0% | 1.9% | 5% | 0% |
| V | w/ lysozyme | | | ✓ | | | | | | lysozyme: |
| W | 65% DDA Chitosan + gelatin | | | ✓ | ✓ | 45% | 45% | 4.0% | 6% | 0% |
| X | 45% DDA chitosan + gelatin | 3 | | ✓ | ✓ | 45% | 45% | 2.7% | 7% | 0% |
| Y | 35% DDA chitosan + gelatin | | | | ✓ | 45% | 45% | 4.0% | 6% | 0% |
| Z | 20% DDA chitosan + gelatin | 4 | | ✓ | ✓ | 45% | 45% | 5.0% | 5% | 0% |
| AA | Lysozyme, only | | | ✓ | ✓ | n/a | n/a | n/a | n/a | 100% |
| AB | Glucosamine-HCl | 5 | | | ✓ | n/a | n/a | n/a | n/a | 100% |
| AC | Surgicel | | | | ✓ | n/a | n/a | n/a | n/a | 100% |
| AD | Surgical Sham | n/a | ✓ | | | n/a | n/a | n/a | n/a | n/a |
| AE | Gelfoam + thrombin | 5 | ✓ | | ✓ | n/a | n/a | n/a | n/a | n/a |

Figure 9C.

1a Supplier Direct Deacetylation
1b Supplier Direct Deacetylation, but additionally cleaned at HemCon
2 Supplier UltraPure Direct Deacetylation
3 Supplier UP Direct Deacetylation, THEN reacetylated at HemCon
4 Supplier Pure Direct Deacetylation, THEN reacetylated at HemCon
5 Commercial Source

| Biomaterial Composition and Characteristics | | | | | | | |
|---|---|---|---|---|---|---|---|
| Alpha ID | Molecular weight-Mw (daltons) | Molecular weight-Mn (daltons) | DDA, FT-IR | DDA, NMR | DDA, PUV | Dimensions implanted (l x w x h) | Compression Thickness (mm) | Density (g/cc) |
| S | 101,550 | 50,250 | 42% | n/a | n/a | 2000 mg/kg | n/a | n/a |
| T | 23,995 | 16,385 | n/a | n/a | n/a | 2040 mg/kg | n/a | n/a |
| U | 95,370 | 46,604 | 33% | n/a | n/a | 2000 mg/kg | n/a | n/a |
| V | 19,660 | 13,686 | n/a | n/a | n/a | 2040 mg/kg | n/a | n/a |
| W | n/a | n/a | 67% | n/a | n/a | n/a | 1mm | 0.28 |
| X | n/a | n/a | 45% | n/a | n/a | n/a | 1mm | 0.28 |
| Y | 95,370 | 46,604 | 33% | n/a | n/a | n/a | 1mm | 0.28 |
| Z | n/a | n/a | 19% | n/a | n/a | n/a | 1mm | 0.28 |
| AA | 14,000 | n/a | n/a | n/a | n/a | 40 mg/kg | n/a | n/a |
| AB | 215 | n/a | 100% | n/a | n/a | 2000 mg/kg | n/a | n/a |
| AC | n/a | n/a | n/a | n/a | n/a | 10mm x 5mm x <1mm | n/a | n/a |
| AD | n/a | n/a | n/a | n/a | n/a | n/a | n/a | n/a |
| AE | n/a | n/a | n/a | n/a | n/a | n/a | n/a | n/a |

Figure 9D.

Table of Rat Implantation Study Compositions with Biocompatibility following Bioabsorption

| ID | Biomaterial | Dermal Lesions | Histopathology: 28 day observation | Fragmentation: % of test article 'n' that fragmented | |
|---|---|---|---|---|---|
| | | | | 8-day | 28-day |
| Test conditions | | | | | |
| A | 63% DDA chitosan + gelatin x-link | No | > (-) Thick fibrotic capsule without ingrowth into bulk.<br>> (-) No host response within bulk.<br>> (-) Cell and tissue fragments at interface.<br>> Abundant giant cells.<br>> Test article fragments within capsule. | 0% | 0% |
| B | 63% DDA chitosan + gelatin | Yes | > (-) Filamentous test article with minimal fibrotic ingrowth.<br>> (-) Fibrotic response limited to periphery with thick fibrous capsule with test article fragments.<br>> (-) Cell and tissue debris at interface.<br>> (-) No host response within bulk. | ne | 88% |
| C | 63% DDA chitosan | Yes | > (-) No ingrowth into bulk.<br>> (-) Cell and tissue debris at interface.<br>> Test article surrounded by thick capsule with test article fragments. | 0% | 75% |
| E | 88% DDA chitosan + gelatin | No | Not evaluated (ne) | ne | 33% |
| F | 63% DDA chitosan + gelatin +lactic | Yes | Not evaluated (ne) | ne | 75% |
| G | 63% DDA chitosan + gelatin | Yes | Not evaluated (ne) | ne | 88% |
| H | 63% DDA chitosan washed | Yes | Not evaluated (ne) | 0% | ne |
| I | Mdoc + 63% DDA chitosan | Yes | Not evaluated (ne) | 0% | ne |
| K | reacetylate 88% DDA to ~35% DDA | No | > (+) Filamentous test article with peripheral fibrosis + giant cells ingrowth.<br>> (+) Moderate fibrotic giant cell capsule with test article fragments<br>> (+) Central 50-80% area of sample is tissue fluid. | 0% | 0% |
| M | reacetylated 88% DDA sponge to chitin | No | > (+) Interstices between test article is filamentous and almost filled with fibrotic response.<br>> (+) Thin to moderate fibrous capsule with test article fragments.<br>> (+) Filamentous test article with peripheral fibrosis + giant cells ingrowth.<br>> (+) Central 80% area of sample is tissue fluid.<br>> Small central area without fibrosis | 0% | 0% |
| Control conditions | | | | | |
| AC | Surgicel | No | Not evaluated | 0% | 0% |
| AD | No biomaterial | No | not relevant (n/a) as sham surgery used | n/a | n/a |

Figure 10.

MLT testing & results of chitosan material compositions

| Ref | Test Sample extracts in Normal Saline | % DDA | MW Result | AST/MLT Result | Pilo-erection | Leth-argy | Weight loss | Hair loss | Lesion | Death |
|---|---|---|---|---|---|---|---|---|---|---|
| V | Reacetylated UP Chitosan + lysozyme + acid | ~35% | 19,600 | PASS | No | No | No | No | No | No |
| U | Reacetylated UP Chitosan + acid | ~35% | 95,370 | PASS | No | No | No | No | No | No |
| L | Reacetylated UP Chitosan + lysozyme + acid | ~35% | 40,000 | PASS | No | No | No | No | No | No |
| T | Reacetylated UP Chitosan + lysozyme + acid | ~45% | 23,995 | FAIL | Yes | Yes | No | Yes | No | Yes |
| S | Reacetylated UP Chitosan + lysozyme + acid | ~45% | 101,550 | Unfavorable result | Yes | No | No | Yes | No | No |
| R | Reacetylated UP Chitosan + lysozyme + acid | ~60% | 35,710 | FAIL | Yes | Yes | Yes | No | No | Yes |
| Q | Reacetylated UP Chitosan + acid | ~60% | 113,230 | Unfavorable result | Yes | No | No | Yes | No | No |
| P | Reacetylated UP Chitosan + lysozyme + acid | ~63% | 35,520 | FAIL | Yes | Yes | ? | Yes | Yes | Yes |
| D | Direct deacetylate Chitosan + lysozyme + acid | ~63% | 34,980 | FAIL | No | No | Yes | Yes | Yes | No |
| N | Reacetylated UP Chitosan + acid | ~88% | 135,850 | Unfavorable result | Yes | Yes | No | No | No | No |
| Z | Glucosamine- HCl + NS | 100% | 215 | PASS | No | No | No | No | No | No |
| Y | Lysozyme only (and acid) | n/a | 14,000 | PASS | No | No | No | No | No | No |

Figure 11.

Hemostatic Efficacy

| HemCon AS Foamed Chitosan:gelatin prototype forms | | *in vivo* Hemostatic Efficacy (Swine Models) | | | | | | | | |
|---|---|---|---|---|---|---|---|---|---|---|
| | | Liver Capsular Stripping, Heparinized | | | Spleen Capsular Stripping, Heparinized | | | Aorta Puncture (not Heparinized) | | |
| ID | Chitosan DDA | P | F | % Success | P | F | % Success | P | F | % Success |
| W | ~65% DDA Chitosan | 6 | 0 | 100% | | | not tested | 3 | 2 | 60% |
| X | ~45% DDA Chitosan | 5 | 0 | 100% | 0 | 2 | 0% | 4 | 0 | 100% |
| Y | ~35% DDA Chitosan | 4 | 2 | 67% | | | not tested | | | not tested |
| Z | ~20% DDA Chitosan | 5 | 3 | 63% | 4 | 1 | 80% | 4 | 0 | 100% |
| Reference/Controls | | | | | | | | | | |
| AC | Surgicel | 1 | 3 | 25% | | | not tested | | | not tested |
| AE | Gelfoam + Thrombin (5000 IU — > 1000/mL) | 4 | 0 | 100% | | | not tested | | | material not suitable for arterial injury |

Figure 12.

Bioresorbability, Biocompatibility & Hemostatic Efficacy

| | | | *in vivo* Hemostatic Efficacy | | |
|---|---|---|---|---|---|
| | | | Anti-coagulated Models (heparinized) | | Arterial Bleeding Model |
| | Implant/ Resorption at 28d | Biocompatibility | Liver, capsular stripping, 2cm round | Spleen, capsular stripping, 1cm round | Abdominal Aorta, puncture, 4mm |
| K, Z: HemCon Chitosan Absorbable Surgical | ~30% decrease in x-sectional area between implant and 28 days[1]. | Very Good- cytotox, acute systemic tox, and irritation assessed | 63% (n=8) | 80% (n=5) | 100% (n=4) |
| Reference/ Control | | | | | |
| AC: Surgicel | Material resorbed by 28 days† | *Not tested by HemCon* | 25% (n=6) | 0% (n=2) | Historically 0% |

1. Implant data @ rat, intraperitoneal, 28 day timepoint. Prototype = biofriendly material. Cellular infiltration seen (positive sign).
†Historically Surgicel resorbs in around 90 days. Suspect migration and not resorption as Surgicel not anchored well to liver injury site.

Figure 13.

BIOCOMPATIBLE AND BIOABSORBABLE DERIVATIZED CHITOSAN COMPOSITIONS

RELATED APPLICATIONS

This application is a continuation of U.S. patent application Ser. No. 14/211,632, filed on Mar. 14, 2014, which itself claims priority to U.S. provisional patent application Ser. No. 61/784,467, filed on Mar. 14, 2013, the contents of which are fully incorporated herein by reference.

STATEMENT REGARDING FEDERALLY SPONSORED RESEARCH OR DEVELOPMENT

This invention was made with government support under Contract DAMD 17-02-C-0095 awarded by U.S. Army Medical Materiel Development Activity and Contract N00014-10-M-0201 awarded by the U.S. Office of Naval Research. The government has certain rights in the invention.

FIELD OF THE INVENTION

The present invention generally relates to biocompatible, bioabsorbable derivatized non-crosslinked chitosan compositions that may or may not be crosslinked to gelatin/collagen by 1-ethyl-3-[3-dimethylaminopropyl]carbodiimide hydrochloride (EDC) for biomedical use and methods of making and testing such compositions. The compositions of the present invention comprise derivatized chitosan reacetylated to a degree of N-deacetylation (DDA) of between about 15% and 40%. As confirmed using a modified acute systemic toxicity test developed by the inventors, the implantation of the present inventive compositions into mammals does not produce toxic biodegradation species giving rise to an elevated cytokine IL-1β response. The inventive compositions are typically bioabsorbed in about 90 days or less and can be made to bioabsorb at differing rates of speed. The inventive compositions are initially soluble in aqueous solution below pH 6.5. The inventive compositions have an acid content that can be adjusted between about 0% (w/w) and about 8% (w/w) to customize the composition for uses that require and/or tolerate differing levels of cytotoxicity, adhesion, composition cohesion, and cell infiltration into the composition.

BACKGROUND OF THE INVENTION

Chitin is a natural high molecular weight polymer widely found in nature. It is the main component of insect and crustacean cuticle, and is also part of the cell walls of some fungi and other organisms. Chitin is generally extracted from its natural sources by treatments with strong acid (to remove calcium deposits where required) and strong alkali (to remove proteinaceous residue). Chitin is insoluble under typical aqueous conditions and is considered to be a relatively intractable polymer (difficult to process). Dissolution of chitin to enable direct processing into fibers or other forms requires the use of unattractive solvent systems that are generally corrosive and toxic.

Chitosan is produced at the industrial level by hydrolytic deacetylation of chitin. Chitin and chitosan are part of the glycosaminoglycan family of polymers. Chitosan is typically derived from chitin by deacetylation in the presence of alkali. Chitosan is a generic term used to describe linear polysaccharides which are composed of glucosamine and N-acetyl glucosamine residues joined by β-(1-4) glycosidic linkages (typically the number of glucosamines ≥N-acetyl glucosamines) and whose composition is soluble in dilute aqueous acid. The chitosan family encompasses poly-β-(1-4)-N-acetyl-glucosamine and poly-β-(1-4)-N-glucosamine with the acetyl residue fraction and its motif decoration (either random or block) affecting chitosan chemistry. The 2-carbon amino group on the glucosamine ring in chitosan allows for protonation, and hence solubilization of chitosan in water (pKa≈6.5) (Roberts). This allows the ready processing of chitosan into fibers, films, and other forms, as well as the ability to prepare high purity chitosan for biomedical use.

Depending on original biological material sourcing and control of processing of chitin to chitosan, poly-N-acetyl-glucosamine compounds exhibit widely differing physical and chemical properties which are processable from aqueous solution. These differences are due to chitosan's varying molecular weights, varying degrees of acetylation, the presence of contaminants such as covalently bound, species-specific proteins, single amino acid and inorganic contaminants, etc.

Much attention has been paid to chitosan as a functional polymer because several distinctive biomedical properties such as non-toxicity, biocompatibility and biodegradability have been reported. Indeed, chitosan is widely regarded as being a non-toxic, biologically compatible polymer. (Kean, T. et al., 2005, Adv. Drug Deliv. Rev. 62:3-11 ("Kean"); Ren, D. et al., 2005, Carbohydrate Res. 340(15):2403-10 ("Ren")).

The potential safe, biocompatible, and bioabsorbable use of chitosan makes it an attractive natural material for use in biomedical implants. Further, deacetylated and partially deacetylated chitin preparations exhibit potentially beneficial chemical properties, such as high reactivity, dense cationic charges, powerful metal chelating capacity, the ability to covalently attach proteins, and solubility in many aqueous solvents. Also, it is conventionally understood that chitosan adheres to living tissue, acts as a haemostatic agent, promotes rapid healing, and has antibacterial properties.

These chemical and biological properties are now beginning to prove useful in many medical applications. Although chitosan compositions are being used increasingly in the United States, Europe, and Asia in external medical applications, such as wound composition products, sponges, powdered haemostatic agents, and antimicrobial gels, biocompatible and bioabsorbable chitosan compositions are yet to be approved for internal surgical use.

Chitosan has not gained usage as a biocompatible and bioabsorbable biomedical implant material, at least in part, because chitosan comprises a large group of structurally different chemical entities and its biodegradation properties are driven by multiple co-dependent factors that render composition design unpredictable. Various physicochemical characteristics of chitosan, such as molecular weight, degree of deacetylation, and distribution of acetamide groups in the chitosan molecule, influence chitosan function and bioabsorbability. (Kofuji, K. et al., 2005, Eur. Polymer J. 41:2784-2791 ("Kofuji")). Of these characteristics, molecular weight and the degree of N-deacetylation (DDA) are believed to be the two most important determinants of the bioabsorbability properties of chitosan. (Ren; Kean).

The in vivo degradation of chitosan is not fully understood but it is believed to occur by enzymatic cleavage of the polymer chain. (Kean; Ren). Lysozyme is the most prominent of the chitosan degrading enzymes in humans, however there are various other chitanases generally found in animals, plants, and microbes. (Kean). The degradation behavior of chitosan plays a crucial role in biocompatible material performance. The degradation kinetics may affect many cellular processes, including cell growth, tissue regeneration, and host response. (Ren). Investigations regarding the degradation of chitosan by lysozyme indicate that the DDA of chitosan is one of the key factors controlling the degradation of chitosan. (Id.). Also, it has been noted that N-substitution may affect enzymatic degradation. (Kean).

The rate of biodegradation and bioabsorption in vivo is also subject to the competing process of foreign body encapsulation (fibrous capsule formation) which may ultimately wall-off the bioabsorbing composition if the rate of its bioabsorption is sufficiently slow and the foreign body elicits a moderate inflammatory response to promote an enhanced rate of encapsulation. Such encapsulation is undesireable for an intended bioabsorbable composition since it can extend the residence time of the composition in vivo potentially from months to years. A reduced rate of encapsulation combined with timely clearing and removal of the foreign body is desired since protracted residence time can result in the adverse events of vascular and/or neural impingement as well as promote infection.

A prerequisite for effective scission of chitosan by lysozyme is that there are regular groupings of at least three consecutive N-acetyl glucosamine monomers in the polysaccharide chain (Aiba), i.e., the DDA of chitosan is sufficiently low (<70% DDA) with the necessary N-acetyl motif structure to enable systematic enzymatic cleavage. Generally, the more acetyl groups on the chitosan, the faster its degradation rate. (Tomihata, K. et al., 1997, Biomaterials 18:567-575 ("Tomihata")).

The water soluble range for chitosan above pH 6.5, which is between 45% and 55% DDA (Roberts 1992), often causes confusion in the determination of absolute rates of scission and of bioabsorption since water soluble chitosan will appear to bioabsorb more quickly when in fact it has only dissolved. (Freier, T. et al., 2005 Biomaterials, 26 (29): 5872-8 ("Freier")).

As a general matter in addition to its DDA, other chitosan molecule characteristics such as its molecular weight, viscosity, solubility, and distribution of acetamide groups affect chitosan's bioabsorption properties.

Also, as indicated previously, biomaterial biocompatibility plays an important role in bioabsorption. Biomaterials which are biodegradable by enzymatic, hydrolytic or oxidative pathways, but which only slightly elevate the local biomaterial inflammatory response, will bioabsorb at a slower rate than biodegradable biomaterials that moderately elevate the same response. Interestingly, chitosan at high DDA is shown to have very good biocompatibility, with reported biocompatibility declining as DDA is reduced. (Tomihata).

It is conventionally understood that chitosan bioabsorption and biodegradation requires chitosan with DDA less than 70% and more than 40% DDA if the poly-β-(1-4) N-acetyl glucosamine is to still be considered chitosan (soluble in dilute aqueous solution). Pure chitin (DDA near 0.0) has shown to be bioabsorbable. (Tomihata). Chitosan compositions at about 70% DDA and higher demonstrate minimal biodegradation due, at least in part, to lack of acetyl groups to prompt enzymatic cleavage and/or lack of solubility. (See Freier, T. et al., 2005 Biomaterials, 26 (29): 5872-8 ("Freier")).

It has been found that within a week of implantation that these higher DDA chitosans, while showing very good biocompatibility, begin to experience encapsulation. (Vandevord). As such, chitosan compositions near 70% DDA and higher, with their slow rate of biodegradation and encapsulation, may never fully resorb in vivo, and may produce undesirable encapsulation.

It is reported in the literature that chitosan having below a 70% DDA is demonstrated as biocompatible and bioabsorbable and is proposed as safe for biomedical use. Only chitosan compositions having a DDA of between about 40-70%, however, have been demonstrated to bioabsorb in vivo with the definition of the poly-β-(1-4) N-acetyl glucosamine being chitin or chitosan at the lower DDA being dependent, as per Roberts, on its water solubility at or below pH 6.5. The biocompatibility of these bioresorbable chitosan compositions, although less than high DDA chitosan, has been reported to warrant further investigation. The number of reported in vivo studies of bioabsorption of chitosan with actual bioabsorption occurring, however, is very low. (See e.g., Tomihata). The majority of other studies purporting to study chitosan bioresorption use only in vitro enzymatic conditions (generally lysozyme). As shown, lysozyme solution allows for analysis of the relative susceptibly of chitosan to biodegrade in vivo, however, it cannot account for absorption and biodegradation effects associated with biomaterial biocompatibility and the biocompatibility of the biodegradation products.

The biocompatibility and bioabsorption of chitosan compositions with DDAs lower than 40% have not been widely investigated. This may be, in part, due to the fact that achieving a chitosan with a lower DDA can be difficult. (Ren). Also, lowering the DDA of chitosan below 40% to achieve faster rates of biodegradation is frustrated by the fact that chitosan having a DDA less than 40% should make the chitosan insoluble in aqueous solution below pH 6.5 and hence not chitosan as per the Roberts definition. (See e.g., Ren; Xu, J. et al., 1996, Macromolecules 29:3436-3440 ("Xu"); Freier). Further, chitosans having DDAs below 50% are not typically commercially available.

Nonetheless, to the extent that lowering the DDA of chitosan may beneficially serve to increase its rate of biodegradation, the conventional wisdom is that too fast a rate of biodegradation may be undesirable as it is well-known that the more rapidly biomaterials biodegrade, the more likely they are to elicite an acute inflammation reaction due to a significantly large production of low-molecular-weight compounds within a short time. (Tomihata).

Additionally, preparing compositions to include chitosan having the water soluble range of 45%-55% DDA will cause undesirable swelling and fluid absorption by the compositions that may cause undesirable and unpredictable fluctuations in implant size and performance during bioabsorption.

As detailed below, the inventors of the present invention have surprisingly discovered that, contrary to conventional wisdom and industry practice, compositions comprising derivatized non-crosslinked chitosan compositions with a DDA range between 40% and about 70% are toxic when implanted, biodegraded, and bioabsorbed. The present inventors have also surprisingly discovered that biocompatible, non-toxic and bioabsorbable biomedical chitosan compositions with a DDA range of between about 15% and 40% can be prepared that, upon implant, are at least 85% bioabsorbed within about 90 days or less. Accordingly, the present inventors have not only overcome widely held misconceptions by those skilled in the art regarding the biocompatibility and bioabsorbability of compositions comprising chitosan with a DDA range between 40% and about 70%, but they have achieved 1) the surprising identification of a biocompatible and bioabsorbable chitosan DDA range of between about 15% and 40%, 2) methods of making the inventive compositions comprising derivatized non-crosslinked chitosan using chitosan having a DDA range of between about 15% and 40%, and 3) developed a modified acute systemic toxicity test to ensure that the compositions of the present invention, when implanted, do not produce toxic biodegradation species giving rise to an elevated IL-1β cytokine response.

BRIEF SUMMARY OF THE INVENTION

The present invention relates, first, to biomedical biocompatible and bioabsorbable compositions comprising derivatized non-crosslinked chitosan with a DDA range between about 15% and 40% with the derivatized non-crosslinked chitosan of that composition at least initially soluble in aqueous solution at pH 6.5. The compositions of the present invention are specifically intended for simple aqueous preparation of bioabsorbable and biocompatible implantable constructs with complete biodegradation and bioabsorption within about 90 days or less. By enabling ease of aqueous construct preparation (fiber, film, freeze-dried matrix, etc.) and acceptably rapid controlled bioabsorption of a biocompatible material, the present invention reduces unnecessary risk to a recipient since prolonged presence of an inflammatory foreign body or one that does not absorb can cause adhesion, encapsulation, and/or infection.

The present invention further relates to methods of making biocompatible, bioabsorbable compositions comprising derivatized non-crosslinked chitosan (that may or may not be crosslinked to Gelatin/Collagen by EDC) with a DDA range between about 15% and 40% for biomedical use. In one embodiment, the compositions of the present invention are prepared by reacetylation of chitosan that has been deacetylated to a DDA of about 80% or higher in acetic acid to achieve a DDA range between about 25% and 40%. Specifically, reactivation from a pure high DDA chitosan of between about 85% and 100% is preferred. In addition to direct reacetylation, the methods of the present invention may optionally include reduction of chitosan free amine functionality by reaction with an electrophile.

The inventive compositions are made so as to be at least initially soluble in aqueous solution below pH 6.5.

The term "chitosan" as used in the compositions of the present invention refers to chitosan that is, at least initially, soluble in an aqueous solution having a pH below or at about 6.5. It is noted that the chitosan included in the compositions of the present invention may at some point become insoluble, but that the insoluble material is nonetheless continuously referred to as chitosan throughout this disclosure based on its initial solubility in an aqueous solution having a pH below or at about 6.5. Accordingly, disclosed herein are inventive compositions which comprise chitosan and that may or may not, at some point, include an insoluble chitosan material.

The inventive compositions have an adjustable acid content of between about 0% (w/w) and about 8% (w/w) which can be customized based on its intended use and depending on requirements and/or tolerance of differing levels of cytotoxicity, adhesion, composition cohesion, and cell infiltration into the composition.

Additionally, the present invention further relates to methods of testing such compositions. Specifically, the present inventors have developed a modified Acute Systemic Toxicity (AST) Mouse Lesion Test (MLT) to ensure that the implantation of the present inventive compositions into mammals does not produce toxic biodegradation species giving rise to an elevated cytokine IL-1β response. The AST MLT involves a partially lysozyme biodegraded chitosan that is predictive of chitosan bioabsorption toxicity.

The compositions of the present invention may be used in biomedical applications including, but not limited to, use in surgery, minimally invasive procedures (endoscopic and laparoscopic), hemostasis control, tissue filling, scaffolding, tissue regeneration, adhesion prevention, and drug delivery.

The compositions of the present invention may take several physical forms including, but not limited to, sponges, membranes, scaffolds, films, gels, injectable gels and/or fluids, fibers, nanofibers, powders, etc.

The present inventive compositions overcome widely held and problematic misconceptions regarding the safety and biocompatibility of compositions comprising chitosan with a DDA of between 40% to about 70%, i.e., that such compositions provide improved biocompatible and bioabsorbable implant compositions. For the first time, the inventors have surprisingly discovered safe, biocompatible, and bioabsorbable compositions for implant comprising chitosan having a DDA range of between about 15% to 40%. The inventors' identification of this lower chitosan DDA range for biocompatible bioabsorbable internal use debunks not only misconceptions regarding the safety of chitosan with a DDA of between 40% to about 70%, but also works in opposition to various other factors known to those skilled in the art that have made attempts to develop such compositions undesirable such as, solubility problems, lack of predictability, etc.

BRIEF DESCRIPTION OF THE DRAWINGS

The accompanying drawings, which are incorporated in and constitute a part of this specification, illustrate various exemplary embodiments.

FIG. 1A shows a chitosan +20% acid (w/w) sample. FIG. 1B shows a chitosan with no acid sample.

FIGS. 8A, 8B, 8C, and 8D. System of ranking extent of atopic dermatitis lesions in rats and mice (images of lesions) following intraperitoneal introduction of bioabsorbed chitosan.

FIGS. 9A, 9B, 9C, and 9D. Material Compositions and Key Alpha Identifier Index.

FIG. 10. Rat Implantation Study Compositions With Biocompatibility Following Bioabsorption.

FIG. 11. MLT Testing And Results Of Chitosan Material Compositions.

FIG. 12. Table of Hemostatic Efficacy Results.

FIG. 13. Bioabsorbability, Biocompatibility, And Hemostatic Efficacy.

DETAILED DESCRIPTION OF THE INVENTION

A. Compositions

Figure 1A:
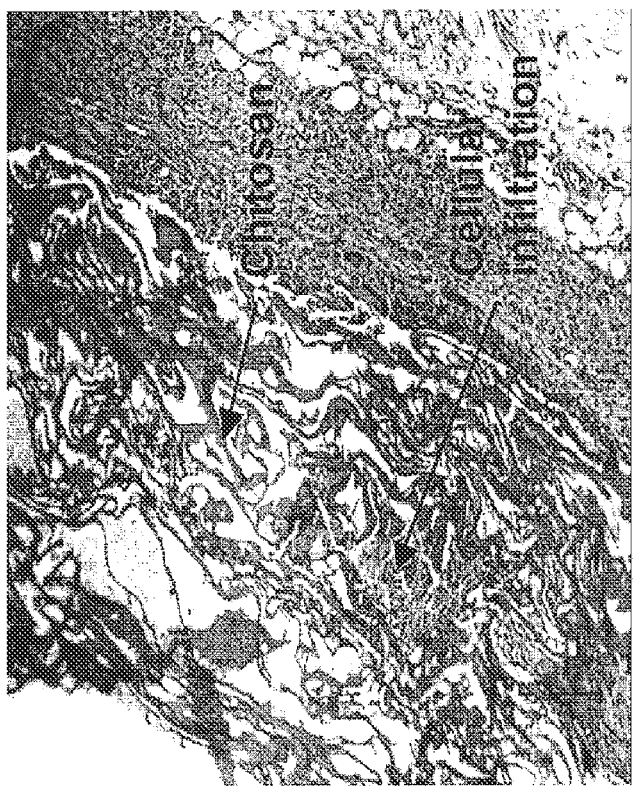
FIGS. 1A and 1B. Slides showing histopathology of subcutaneous implanted material (rat) seven days after implantation.

Chitosan used in the present invention may be from any source. Industrial production of chitosan generally exploits crustacean shell wastes, for instance crab or shrimp shells. Alternative sources for chitosan include, for example, fungi and other industrial fermentation process by-products, such as the biomass collected after fungi or yeast fermentation.

The chitosan starting materials used in the present invention may be high quality medical grade chitosans derived from shrimp and qualified according to ASTM F 2103-01. Preferably, the chitosan starting material is at least about 75% to 100% deacetylated, more preferably the chitosan starting material is at least about 85% to 100% deacetylated, and still more preferably the chitosan starting material is at least about 95% to 100% deacetylated.

The chitosan starting material can be of pharmaceutical grade or equivalent quality, e.g., ultrapure FMC Novamatrix chitosan and acetylated ultrapure FMC Novamatrix chitosans. Advantageously, the chitosan may be pharmaceutical grade, prepared and processed according to GMP (good manufacturing practice) standards. The chitosan should not contain excessive levels of heavy metals, proteins, endotoxins or other potentially toxic contaminants. The dry starting chitosan material should be at least 99% pure and demonstrate absence of heavy metals (Pb+Hg+Cd+As<500 ppb); undetectable residual protein (<200 ppm); and low endotoxin (preferably <100 EU/g, more preferably <20 EU/g, and most preferably <5 EU/g).

The chitosan starting material used with the present invention should have a weight average molecular weight of at least about 80 kDa, more preferably, it has a weight average molecular weight of at least about 250 kDa, and most preferably, it has a weight average molecular weight of at least about 150 kDa.

Preferably, the chitosan starting material has a viscosity (which is about 100 centipoise to about 2,000 centipoise) at 25° C. in 1% w/w solution in 1% w/w acetic acid (AA) with spindle LV1 at 30 rpm. More preferably, the chitosan has viscosity (which is about 125 centipoise to about 1,000 centipoise) at 25° C. in 1% w/w solution in 1% w/w acetic acid (AA) with spindle LV1 at 30 rpm. Most preferably, the chitosan has viscosity (which is about 150 centipoise to about 500 centipoise) at 25° C. in 1% solution w/w in 1% w/w acetic acid (AA) with spindle LV1 at 30 rpm.

In the case of chitosan starting material: preferably, undissolved solid in a 1% w/w chitosan solution in 1% acetic acid at 25° C. is ≤10% w/w. More preferably, undissolved solid in a 1% w/w chitosan solution in 1% acetic acid at 25° C. is ≤2% w/w. Most preferably, undissolved solid in a 1% w/w chitosan solution in 1% acetic acid at 25° C. is ≤1% w/w.

In one embodiment, the deacetylated chitosan starting material is reacetylated to achieve the compositions of the present invention. Reacetylation of the deacetylated chitosan beneficially enhances control of levels of deacetylation below 40% DDA, aids removal of undesirable residual proteinaceous epitopes, and produces a more desirable controlled material. Reacetylation from a pure high DDA chitosan of about 85%-100% DDA is preferred since (1) the more robust deacetylation treatment will more likely remove undesirable proteinaceous epitopes, (2) chitosan materials can be filtered since chitosan is soluble, (3) reacetylation of solubilized chitosan provides for more reproducible random chitosan structure, and (4) the DDA range will be more uniform (less likelihood of presence of toxic biodegradation residue).

The reacetylated chitosan material used with the present invention should have a weight average molecular weight of at least about 90 kDa, more preferably, it has a weight average molecular weight of at least about 280 kDa, and most preferably, it has a weight average molecular weight of at least about 170 kDa.

Preferably, the reacetylated chitosan starting material has a viscosity (which is about 100 centipoise to about 2,000 centipoise) at 25° C. in 1% w/w solution in 1% w/w acetic acid (AA) with spindle LV1 at 30 rpm. More preferably, the chitosan has viscosity (which is about 125 centipoise to about 1,000 centipoise) at 25° C. in 1% w/w solution in 1% w/w acetic acid (AA) with spindle LV1 at 30 rpm. Most preferably, the chitosan has viscosity (which is about 150 centipoise to about 500 centipoise) at 25° C. in 1% w/w solution in 1% w/w acetic acid (AA) with spindle LV1 at 30 rpm.

Purity of the reacetylated chitosan material is determined by infrared analysis, preferably with demonstration of absence of the O-acyl absorption at $1740 \pm 10$ cm$^{-1}$ and determination of residual moisture. The presence of small residual levels of o-acetylation should not significantly affect biocompatibility or efficacy. Its control provides a level of impurity control in the target derivatized chitosan for regulatory purposes.

The dried reacetylated chitosan can become insoluble if heated at temperatures above 40° C. and if stored for more than seven days at room temperature. Preferably the material is dried by lyophilization at less than 20° C. to near 5% w/w residual moisture. If more than seven days of storage is required, then preferably it should be stored at between 2° C.-8° C. or, more preferably, at −20° C. or below.

The following solubility profile is desired in the case of reacetylated chitosan. Preferably, undissolved solid in a 1% w/w chitosan solution in 1% acetic acid at 25° C. is ≤10% w/w. More preferably, undissolved solid in a 1% w/w chitosan solution in 1% acetic acid at 25° C. is ≤2% w/w. Most preferably, undissolved solid in a 1% w/w chitosan solution in 1% acetic acid at 25° C. is ≤1% w/w.

The reacetylated chitosan preferably has a DDA range of at least about 15% to 40%, preferably about 15% to 35%, more preferably of at least about 20% to 35%, and most preferably at least about 20% to 30%.

Here, "DDA" or "degree of deacetylation" is defined to refer to the final proportion of amino groups in the 2-position of the D-glucosamine (D-glucopyranose) units constituting the chitosan (or poly-β-(1-4)-N-acetyl-D-glucosamine or poly-β-(1-4)-2-acetamido-2-deoxy-D-glucopyranose), which have been converted to free amino groups by deacetylation or any combination of deacetylation with reacetylation and/or substitution involving an electrophile. 100% DDA chitosan (poly-β-(1-4)-D-glucosamine or poly-β-(1-4)-2-amino-2-deoxy-D-glucopyranose) results from removal of all acetyl (acetamido) functionality at the 2-position of the D-glucosamine.

Typically these electrophile/nucleophile (Lewis acid-base) reactions provide for amide formation, N-acylation, carboxylation and alkylation of the C-2 amine.

DDA according to the present invention is measured as determined by FTIR spectroscopic analysis. Baxter, A. et al., 1992, Int. J. Biol. Macromol. 14:166-169 ("Baxter"); Miya, M. et al., 1980, J. Biol. Macromol. 2(5):323-324 ("Miya"); Roberts, G. A. F., 1992, London: MacMillan 86-91 ("Roberts"). This FTIR method provides an accuracy of DDA determination of near ±3% DDA. Although the FTIR method was used predominantly in this invention, alternate techniques to determine DDA were used to corroborate FTIR analyses. The other techniques used were $^1$H NMR (ASTM F2260-03) and UV spectrophotometric determination of DDA using concentrated phosphoric acid as solvent (Hein 2008).

According to an embodiment, the bioabsorbable composition of the present invention, on wetting, has a pH that is compatible with internal use, preferably an initial pH between 5.5 and 7.5, which equilibrates within 24 hours to physiologic pH near pH 7.4.

According to an embodiment, the composition is at least 85% bioabsorbed within about 100 days or around 14 weeks, of implant. In another embodiment, the composition is bioabsorbed within about 60 days, or nine weeks, of implant. In another embodiment, the composition is at least 85% bioabsorbed within about 30 days, or four weeks, of implant. In another embodiment, the composition is at least 85% bioabsorbed within about 14 days, or two weeks, of implant. In another embodiment, the composition is at least 85% bioabsorbed within about seven days, or one week, of implant.

In an embodiment, the chitosan composition further comprises gelatin or collagen. Use of high purity gelatin or collagen is a preferred agent to foam the chitosan gel. Gelatin (porcine source) was obtained from Gelita and contained endotoxin less than 90 EU/g. The gelatin had a 286 g bloom, 5.54 pH, 0.01% ash content, and less than 100 cfu/g bioburden. In a preferred embodiment, a composition comprising chitosan and gelatin is foamed and prepared in connection with lyophilization to make a low density foam sponge. Gentle compression of this foam sponge produces a highly compliant, adherent composition. Chitosan compositions in a preferred embodiment demonstrated acceptable levels of swelling in length and width of not more than 20% on implantation. Depending on the original sponge thickness dimension before thermal compression, thickness of the composition on implantation over 7-14 days may revert to the original sponge thickness. Implantation of compositions according to this preferred embodiment that contain residual acid in the range 0-8% (w/w) resisted dissolution and were effective in controlling robust levels of bleeding.

The compositions of the preset invention may further comprise additional hydrophilic polymers and/or less hydrophilic polymers. The additional polymer may include, but is not limited to, collagen, collagen derivative, gelatin, alginate, chitosan, keratin, a hydrophilic polyamine, a hydrophilic polyamine salt, polydiallyldimethylammonium salt, polyhexamethylene biguanide, polyaminopropyl biguanide, a chitosan derivative, polylysine, polyethylene imine, xanthan, carrageenan, quaternary ammonium polymer, chondroitin sulfate, a starch, a modified cellulosic polymer, a dextran, hyaluronan, carbopol, polyvinyl pyrrolidone, hydrogenated vegetable oil, paraffin, polyethylene-oxide, polyvinylalcohol, polyvinylacetate, pullulan, pectin or combinations thereof. The starch may include, but is not limited to, amylase, amylopectin and a combination of amylopectin and amylase. The modified cellulosic polymer may include, but is not limited to, ethylcellulose, methylcellulose, hydroxypropylcellulose, hydroxypropylmethycellulose, hydroxyethycellulose, carboxymethylcellulose, oxidized cellulose or combinations thereof.

The compositions of the present invention may further comprise an active ingredient. The active ingredient may include, but is not limited to, calcium, albumin, fibrinogen, thrombin, factor VIIa, factor XIII, thromboxane A2, prostaglandin-2a, activated Protein C, vitronectin, chrondroitin sulfate, heparan sulfate, keratan sulfate, glucosamine, heparin, decorin, biglycan, testican, fibromodulin, lumican, versican, neurocan, aggrecan, perlecan, lysozyme, lysly oxidase, glucose oxidase, hexose oxidase, cholesterol oxidase, galactose oxidase, pyranose oxidase, choline oxidase, pyruvate oxidase, glycollate oxidase and/or aminoacid oxidase, D-glucose, hexose, cholesterol, D-galactose, pyranose, choline, pyruvate, glycollate, aminoacid, epidermal growth factor, platelet derived growth factor, Von Willebrand factor, tumor necrosis factor (TNF), TNF-alpha, transforming growth factor (TGF), TGF-alpha, TGF-beta, insulin like growth factor, fibroblast growth factor (FGF), keratinocyte growth factor, vascular endophelial growth factor (VEGF), nerve growth factor, bone morphogenic protein (BMP), hepatoma derived growth factor (HDGF), interleukin, amphiregulin, retinoic acid, erythropoietin, mafenide acetate, silver sulfadiazine, silver nitrate, nanocrystalline silver, penicillin, ampicillin, methicillin, amoxicillin, clavamox, clavulanic acid, amoxicillin, aztreonam, imipenem, streptomycin, kanamycin, tobramycin, gentamicin, vancomycin, clindamycin, lincomycin, erythromycin, polymyxin, bacitracin, amphotericin, nystatin, rifampicin, tetracycline, doxycycline, chloramphenicol, cefuroxime, cefradine, flucloxacillin, floxacillin, dicloxacillin, potassium clavulanate, clotrimazole, cyclopiroxalomine, terbidifine, ketoconazole, paclitaxel, docetaxel, imatinib, exemestane, tamoxifen, vemurafenib, ipilimumab, dacarbazine, interleukin-2, abiraterone, doxorubicin, 5-fluorouracil, tamoxifen, octreotide, sorafenib, resveratrol, ketamine, diclofenac, ibuprofen, paracetamol, codeine, oxycodone, hydrocodone, dihydromorphine, pethidine, buprenorphine, tramadol, venlafaxine, flupirtine, carbamazepine, gabapentin, pregabalin, lidocaine, autologous cell lines, stem cells, and combinations thereof.

The present invention may be accomplished according to various methods and the composition may comprise various forms, including but not limited to freeze-dried sponge, tissue scaffolds, matrix, fiber, powder, sheet, film, membrane, nanofiber, nanoparticle and hydrogel. The compositions of the present invention may be deployed as either standalone implantable rapidly absorbable devices or as rapidly absorbable surface coatings on implantable devices. In part due to the antibacterial nature of chitosan, implant of the absorbable compositions of the present invention may beneficially also allow for the elimination or reduction of ambient contamination that could cause secondary infection.

The rates and quality of biodegradation and bioabsorption of the compositions of the present invention may be assessed using various methods. For example, the rate of bioabsorption may be determined using visual assessment and/or measurement regarding the amount of implanted material that remains over time. Determination of the estimated bioabsorption rate for a medical device for a particular application location in vivo requires implantation in that location of a similar size test composition in thickness (and otherwise having uniform dimensions). Relative density or change in thickness cross-section is determined along the test composition in at least two animals per time point and across at least three time points in which percentage change is more than 50%. Bioabsorption is considered achieved when 85% or more of the test composition has been absorbed. This testing assumes that the test composition generally degrades uniformly from the surface into the bulk and that it does not fragment into large (≥100 microns) pieces that subsequently migrate away from the implant site. Such fragmentation during bioabsorption is undesirable. Testing also assumes that the loss of material is associated with biodegradation and is not by simple dissolution. There are a number of guidelines for performing in vivo biodegradation/bioabsorption studies: ASTM F2150-07 "Standard Guide for Characterization and Testing of Biomaterial Scaffolds Used in Tissue-Engineered Medical Products", ASTM F1983 "Practice for Assessment of Compatibility of Absorbable/Resorbable Biomaterials for Implant Applications", ISO 10993-9 "Biological Evaluation of Medical Devices—Pt 9: Degradation of Materials Related to Biological Testing". The in vivo testing used in the examples below for chitosan bioabsorption was guided by the principles outlined in ASTM F2150-07, ASTM F1983 and ISO 10993-9.

Note that there is acceptance and guidance for standard hydrolytic testing in the case of biomaterials which biodegrade by hydrolysis: ASTM F1635 "Test Method for in vitro Degradation Testing of Hydrolytically Degradable Polymer Resins and Fabricated Forms for Surgical Implants." This is because hydrolysis is simple to model and can be readily controlled. In the case of those biomaterials that biodegrade enzymatically or by phagocytosis such as in the case of chitosan, in vitro testing can provide a helpful guidance to what might be expected, however until in vivo studies for a particular implant location are performed to corroborate in vitro testing results, the in vitro test results cannot be considered reliable indicators of bioabsorption rate.

Non-toxicity according to the present invention may be assessed using various standard methods during/after bioabsorption-biodegradation of the chitosan. Replication of bioabsorption-biodegradation chemical change in vivo is possible using lysozymal enzymatic pretreatment of the chitosan. Subsequent testing of the degraded chitosan in standard biocompatibility assays such as the MEM elution test and/or the Acute Systemic Toxicity test allow for rapid screening of toxicity. As described in section (C) below, the present inventors have developed a modified acute systemic toxicity test to detect an elevated cytokine IL-1β response after implantation of compositions prepared in accordance with the present invention.

In a particularly preferred embodiment, the compositions of the present invention are in the form of a sponge that has been freeze-dried and compressed.

In a particularly preferred embodiment, a freeze-dried sponge according to the present invention comprises derivatized chitosan with a DDA of about 15% to 40% and gelatin that are combined and foamed prior to being freeze-dried. The ratio of chitosan to gelatin in this inventive embodiment may be any of 1:1, 2:1, 3:1, with a preferred ratio for hemostatic composition application being 3:1, a more preferred ratio being 2:1, and the most preferred ratio being 1:1.

The sponge embodiment of the present invention includes about 40% to about 100% w/w, preferably about 45% to about 85% w/w, more preferably about 50% to about 75% w/w, even more preferably about 50% to about 65%, most preferably about 50% to about 55% w/w of the chitosan derivative material.

In an alternative embodiment, a foamed chitosan gelatin sponge may comprise about 40% to about 100% w/w, preferably about 45% to about 85% w/w, more preferably about 50% to about 75% w/w, even more preferably about 50% to about 65%, most preferably about 50% to about 55% w/w of the chitosan derivative material and about 0% to about 60% w/w, preferably about 15% to about 55% w/w, more preferably about 25% to about 50% w/w, even more preferably about 35% to about 50%, and most preferably about 45% to about 50% w/w of the gelatin material.

The inventive compositions may have an adjustable acid content of between about 0% and about 8% which can be customized based on its intended use depending on requirements and/or tolerance of differing levels of cytotoxicity, adhesion, composition cohesion, and cell infiltration into the composition. Preferred acids include acids such as, acetic, carbonic, lactic, glycolic, citric, succinic, malic, glutamic, ascorbic, hydrochloric, malonic, glutaric, adipic, pimelic, tartaric, etc.

The inventive compositions have numerous biomedical applications, including, but not limited to, use in surgery, minimally invasive procedures (endoscopic and laparoscopic), hemostasis control, infection control, tissue filling, scaffolding, tissue engineering, tissue regeneration, controlled delivery of active agents, controlled drug delivery and adhesion prevention and/or combinations of these.

B. Methods of Making Compositions According to the Present Invention

Various methods to achieve the production of chitosan having a DDA of about 15% to 40% are known to those of ordinary skill in the art. However, the inventors have advantageously developed a reacetylation chemistry technique that allows for a one step process to create chitosan having a DDA of between about 15% and 40%. When starting with a high purity chitosan form having a DDA of 75% to 100% and a purity of 99% to 99.99999% this beneficially facilitates production of bioabsorbable chitosan implant materials with controllable and specific degradation profiles.

Accordingly, in a preferred embodiment, preparation of derivatized chitosan involves a derivatization step of high purity chitosan with the stoichiometric addition (in slight excess) of acetic anhydride to a 2% solution of chitosan having a DDA of 80% or more in acetic acid. After reaction of the acetic anhydride with the chitosan to acetylate the chitosan to between about 15% to 40% DDA (as determined by FTIR spectroscopic analysis) the chitosan is raised to pH 13 by addition of 10 M NaOH aqueous solution. This increase to high pH causes the chitosan to precipitate as a slurry and results in the hydrolysis of any chitosan O-acetyl esters. The NaOH and NaAcetate are subsequently removed by washing or by dialysis with multiple changes of water until the conductivity of the chitosan slurry is near the conductivity of the water (near 1 microSiemans/cm). The N-acetyl derivatized chitosan having a DDA between about 15% to 40% may be resolubilized into aqueous solution preferably by use of acetic acid. Once in aqueous solution, the chitosan may be processed into different physical forms. The N-acetylation derivatization of chitosan as described previously is a subset of N-acylation of chitosan in which N-formyl, N-acetyl, N-chloroacetyl, N-ethyl, N-propyl, N-propionyl, N-isopropyl, N-(2-methylproprionyl), N-hydroxyethyl, N-succinyl, N-pentanoyl, N-carboxy, N-carboxymethyl, N-butyryl, N-(2,2-dimethylproprionyl), N-(3-methylbutyryl), N-(3,3-dimethylbutyryl), N-sulfonyl, N,N-dicarboxymethyl, N-butyl, N-pentyl and/or N-hexyl acyl modifications might be made to chitosan to achieve similar effect. Other generic chemical modifications involving nucleophile/electrophile reaction of the glucosamine C-2 nitrogen would include N-alkylation, N-alkylidene/N-arylidene derivitization, and metal chelation.

An alternate method of removal of excess acetic acid after the reacetylation step is to pour the reacetylated chitosan acid solution to a depth of 0.5" in 1.2" deep wells of Teflon™ coated aluminum molds, place the molds on flat stainless steel freeze drier shelf at −40° C. and freeze the solution before freeze-drying to sublimate all the free water and acetic acid over a 48 hour drying cycle. This freeze-drying preparation of the acetylated chitosan provides for a sponge with residual salt bound acetic acid that can be removed, if desired, by the volatilization of acid under heat and humidity. This approach circumvents the need to neutralize with base (NaOH or KOH) and subsequently to remove the base by washing in large quantities of WFI (water for injection). A possible limitation of this approach is that if O-acetylation of the glucosamine/N-acetyl glucosamine has occurred (as evidenced by IR absorbance at 1740±10 cm-1) this may need to be treated by base (NaOH or KOH) to remove the ester or else the presence of this ester would need to be controlled and the O-ester chitosan material validated that it does not change the safety and efficacy profile of the chitosan.

In an alternative embodiment, the derivatization step involves reacetylation of the chitosan having a DDA 80% or more by the method described above to at least as low as about 65% DDA, and then reducing the percentage of chitosan free amine functionality even further to between about 15% and 40% by derivitization of the glucosamine C-2 nitrogen with an electrophile. The N-acetylation derivitization of chitosan as described previously is a subset of N-acylation of chitosan in which N-formyl, N-acetyl, N-chloroacetyl, N-ethyl, N-propyl, N-propionyl, N-isopropyl, N-(2-methylproprionyl), N-hydroxyethyl, N-succinyl, N-pentanoyl, N-carboxy, N-carboxymethyl, N-butyryl, N-(2,2-dimethylproprionyl), N-(3-methylbutyryl), N-(3,3-dimethylbutyryl), N-sulfonyl, N,N-dicarboxymethyl, N-butyl, N-pentyl and/or N-hexyl acyl modifications might be made to chitosan to achieve similar effect. Other generic chemical modifications involving nucleophile/electrophile reaction of the glucosamine C-2 nitrogen would include N-alkylation, N-alkylidene/N-arylidene derivitization, and metal chelation. Generally, performing these reactions is within the knowledge and skill of one skilled in the art.

Because acidic residue in an implantable material can be undesirable as it can lead to acidosis/cytotoxicity, use of acetic acid in casting or freeze-drying of the chitosan compositions is preferred since substantially all of the acetic acid can be removed from the final composition by heating the composition from about 60° C. to about 130° C. Preferably, when removing the final fraction of acetic acid, this heating process is performed with humidity controlled air of about 5% to about 25%. Alternatively, where a certain amount of acid is desired in the composition in order to affect its adhesion properties, acid may be left within the composition in amounts ranging from about 2% w/w to about 8% w/w.

The compositions of dried chitosan derivative compositions are prepared either from a single aqueous acidic chitosan derivative solution or from a combination of an acidic chitosan derivative solution and an aqueous gelatin solution with or without the addition of water-soluble acid. These solutions may also include D-glucosamine, N-acetyl-D-glucosamine, sucrose, lactose, sorbitol, fructose, maltose, dextrose, glucose, polyethylene oxide and glycerol as plasticizers or rheology modifiers. These solutions may also include small amounts of active agents. The acids used to dissolve the chitosan derivative and potentially included as chitosan acid salts in the final compositions may include acids such as acetic, carbonic, lactic, glycolic, hydrochloric, citric, and ascorbic acids, etc. Other examples of acids that may be used include formic (due to toxicity it would need to be fully removed by volatilization), succinic, malic, glutamic, malonic, glutaric, adipic, pimelic, and tartaric acids.

Combined chitosan gelatin solutions are prepared by mass fractional combination of the prepared aqueous solutions of chitosan derivative and gelatin. In the case of gelatin and chitosan derivative solution, EDC may be used in the gelatin chitosan mixture to covalently bind (crosslink) gelatin to chitosan. Foamed compositions of chitosan derivative and gelatin may be prepared by aeration whisking (filtered air of a flow-hood) of the combined gelatin chitosan mixture to a pre-determined lower solution density (e.g., 1.0 g/cm$^3$ to 0.6 g/cm$^3$). Table 1 shows possible compositions of these solutions.

TABLE 1

Materials and Preferred Ranges

| Material | Range % w/w | Preferred range % w/w |
|---|---|---|
| Chitosan/Chitosan Derivative | 0.01-10 | 1-2 |
| Gelatin | 0-10 | 0-1 |
| Acetic acid | 0-80 | 1-4 (Higher amounts of acetic acid reduces chitosan viscosity) |
| Carbonic acid | 0-1 | 0-0.2 |
| Lactic acid | 0-5 | 0-3 |
| Glycolic acid | 0-5 | 0-3 |
| Hydrochloric acid | 0-2 | 0-0.5 |
| Citric acid | 0-1 | 0-0.1 |
| Ascorbic Acid | 0-8 | 0-2 |
| Polyethylene oxide | 0-3 | 0-0.1 |
| Glycerol | 0-3 | 0-0.1 |
| D-glucosamine | 0-1 | 0-0.1 |
| Sucrose | 0-1 | 0-0.1 |
| EDC | 0-0.1 | 0-0.01 |

The final solutions of chitosan derivative in the case of dried compositions, were phase separated and dried. The preferred method of phase separation was by freezing with introduction of a thermal gradient. Typically rectangular aluminum molds 28.5"×4"×1.05" with top recess of 28"×3.5"×0.8" with a thin coating of Teflon™ were placed horizontally on a flat surface and filled to a height of 0.4" with chitosan derivative solution. The mold was then placed on a horizontal shelf which was either pre-cooled to near −45° C. or on the same horizontal shelf near 25° C. which was then ramped at a cooling rate between 0.8° C./min and 2° C./min with final temperature near minus 45° C. (−45° C.). A delay interval of 5 minutes to 60 minutes may be used in the case of the cooling ramp process. The purpose of the delay interval is to moderate the thermal gradient through the 0.4" layer of chitosan to control extent and location of ice nucleation. Alternatively, if the thermal gradient is insufficient to provide for ice nucleation that favors lamella phase separation structure in the frozen cake, the chitosan may initially be heated before loading in the mold or be heated within the mold in the lyophilization to a temperature higher than 25° C. A preferred pre-cooling ramp solution temperature for improved lamella structure is 45° C. A more preferred temperature is 30° C. A most preferred temperature is 35° C. Typically the higher initial temperatures without delay intervals are used in achieving desired freezing structure in high purity chitosan solutions with absence of heterogeneous particles that would normally more readily promote ice nucleation. The solution was left for between 60 to 180 minutes for freezing to be completed. Typically this freezing was performed on a cooling shelf inside the controlled environment of a freeze dryer (e.g. a Virtis™ 24 sqft freeze dryer).

Thermal gradients were achieved in the freezing solution by the directed rapid removal of heat at the mold base surface in direct contact with the cooling shelf and delay in the removal of this heat caused by the relatively high heat capacity of the aqueous solution originally near room temperature, the depth of the same aqueous solution in the mold, and the thermal insulating properties of the solution as liquid and as ice. Once the solution was adequately frozen, sublimation of the ice was achieved by application of both heat and vacuum until residual moisture in the chitosan cake was less than 5% w/w. Typically with vacuum between 100-300 milliTorr, the freeze dryer shelf temperature was gradually increased over 24 to 48 hours to near 25° C.

The increase in temperature was done in such a manner that the original phase separated frozen sponge structure was preserved and there was no occurrence of melt-back phenomena, that is, there was no loss of structure due to cake collapse because of ice becoming liquid. Once achieving a shelf temperature of 25° C., a further 10 to 12 hours of drying was undertaken to ensure adequate uniform dryness of the sponge.

After freeze-drying, the dried sponges near 27"×3"×0.35" were removed for treatment to reduce the volatile acid fraction. If carbonic acid was used to achieve solution and other acids were not present, then no extra treatment was required to remove the acid since the carbonic acid was removed in the freeze-drying step. In the case of other volatile acids, but those less volatile than carbonic acid, typically acetic and lactic acids, the heating of sponges containing these acids at near 80° C. (but also at temperatures between 60° to 130° C.) in a humid environment (5% to 25% humidity) resulted in substantial removal of the volatile acid component. For hemostatic applications, higher density of the original freeze dried sponges (near 0.03 g/cm$^3$) is required to achieve suitable wet mechanical properties of the sponges. Typically this is performed by uniaxial thermal compression of the freeze-dried chitosan sponge at density near 0.03 g/cm$^3$ to a density greater than 0.09 g/cm$^3$ and greater than 0.25 g/cm$^3$, but not greater than 0.5 g/cm$^3$. Preferably, this is performed by uniaxial thermal compression in the temperature range between 60° C. to 85° C., preferably at 80° C., of the freeze-dried chitosan sponge at density near 0.03 g/cm$^3$ to a density greater than 0.07 g/cm$^3$ and preferably greater than 0.12 g/cm$^3$, but not greater than 0.5 g/cm$^3$.

As explained in the examples and in further detail below, the present inventors have discovered that bioabsorption of chitosan composition test samples with a DDA higher than about 45% caused an undesirable level of cytokine response in test rodents which in some instances led to skin lesions and/or systemic atopic dermatitis. The inventors were able to monitor the level of cytokine response in animals receiving implants by determining the presence of IL-1β cytokine in blood samples. The inventors also found that they were able to overcome elevated cytokine response by preparing compositions comprising chitosan having between about a 15% to 40% DDA.

In a particularly preferred embodiment, the inventors advantageously achieved a chitosan composition that is at least 85% bioabsorbed in 90 days or less, demonstrated very good biocompatibility, and good hemostatic efficacy in oozing surgical and high bleeding injuries and anti-coagulation. This preferred embodiment involves an acid mass fraction of about 5% w/w or less and reacetylated chitosan with a DDA of about 40% or less, such as about 15% to about 30%.

C. Modified Acute Systemic Test

The standard acute toxicity test is mouse model (N=5) of systemic toxicity of a test material extract following intraperitoneal injection. The standard test method is described in ANSI/AAMI ISO 10993-11: 2006. Biological Evaluation of Medical Devices. Pt 11. Tests for Systemic Toxicity. The test material extract is obtained by placing the test material (~0.8 g chitosan) of surface area 60 cm$^2$ in 20 ml of standard aqueous saline (9%) at 37° C. for 72 hours. The injected volume of extract is 50 ml extract per kg of body weight (1.0 ml per 20 g mouse).

The modified acute systemic test system was developed as the result of standard biocompatibility testing being found to be non-predictive of severe systemic responses in certain low acid (<5% acetic w/w) chitosans after 3-4 days intraperitoneal implantation (dose≈82 mg/kg, ~14 mg in ~185 g animals) in a rat model. In fact standard (non-implant) ISO 10993 biocompatibility testing, including the acute systemic toxicity test (AST) indicated that the chitosan materials that caused severe systemic reactions on implantation were biocompatible.

The systemic responses observed on implantation involved occurrence of hair loss with skin lesions on tail, foot and face of the rats consistent with atopic dermatitis, as well as loss in appetite, lethargy and loss in weight. Typically the systemic response effects on implantation were found to be present in animals in which chitosan biodegradation occurred. The extent of the systemic response was found to be the greatest in chitosans that biodegraded rapidly on implant. The systemic response was found to present on implantation in chitosans with at least a degree of deacetylation greater than 35% degree of deacetylation and at most a degree of deacetylation less than 70%. The strong systemic response was observed in chitosans with a degree of deacetylation close to 65%. Chitosans close to 65% degree of deacetylation, prepared either by direct deacetylation from chitin (0% degree of deacetylation) or by reacetylation from high purity chitosan near 90% degree of deacetylation, all showed the same severe inflammatory response when implanted. Chitosan near 65% degree of deacetylation that was partially crosslinked with gelatin through the glucosamine C-2 amine, although demonstrating biodegradation on implantation, was not found to cause the atopic dermatitis response in rats, and the rats did not exhibit weight loss or lethargy. The same high degree of deacetylation chitosan that was reacetylated to 35% degree of deacetylation was found to remain soluble in dilute acetic acid solution (able still to be defined as chitosan) and was able to be prepared as a dressing form for use in the rat implantation study. This low degree of deacetylation (35%) was found to biodegrade rapidly on implantation but not demonstrate any of the adverse systemic toxicity responses found in the case of the higher degree of deacetylation chitosan that also degraded rapidly. Reacetylated chitin (near 0% degree of deacetylation) also was prepared. This was insoluble in dilute aqueous acid solution. This reacetylated chitin also demonstrated biodegradation and absence of adverse systemic toxicity.

Blood samples taken from the rats in the implantation study demonstrated that the adverse systemic toxicity correlated with up-regulation of the cytokine IL-1β that is a member of the interleukin 1 cytokine family. This cytokine is produced by activated macrophages as a proprotein, which is proteolytically processed to its active form by caspase 1 (CASP1/ICE). This cytokine is an important mediator of the inflammatory response, and is involved in a variety of cellular activities, including cell proliferation, differentiation, and apoptosis.

The modified AST test included an initial step of treating in lysozyme (0.37% w/w lysozyme solution at 37° C. for 24 hours) to prime the system with degradation products in the case of biodegradable chitosans. In order to dissolve chitosan in the AST elution fluid, residual acetic acid in the test material was generally high (>5% w/w). In order to ensure detection of any systemic effect, high concentrations of test compositions were used (dose≈2000 mg/kg, ~40 mg per ~20 g animal). The normal test window of 3 days for standard AST testing was extended to 7 days for the modified test. Also, additional observational guidelines were added that included monitoring the test animals for pilo-erectile responses, presence of lesions, indications of hair loss, as well as standard lethargy, appetite loss and weight loss. Also a ranking scheme was introduced to grade the severity of the lesions. In the case of the modified AST test, the control saline included 0.37% w/w lysozyme. Generally the modified AST test was run in combination with standard non-degraded (non-lysozyme treated) samples under the same conditions and over the same time period. This allowed for control of any toxicity effect associated with residual acid in the sample.

The examples below are provided for disclosure only and are in no way intended to be limiting on the invention as generally described herein.

Example 1

Reduced Acid Content and Cellular Infiltration in Chitosan Compositions

Figure 1B:
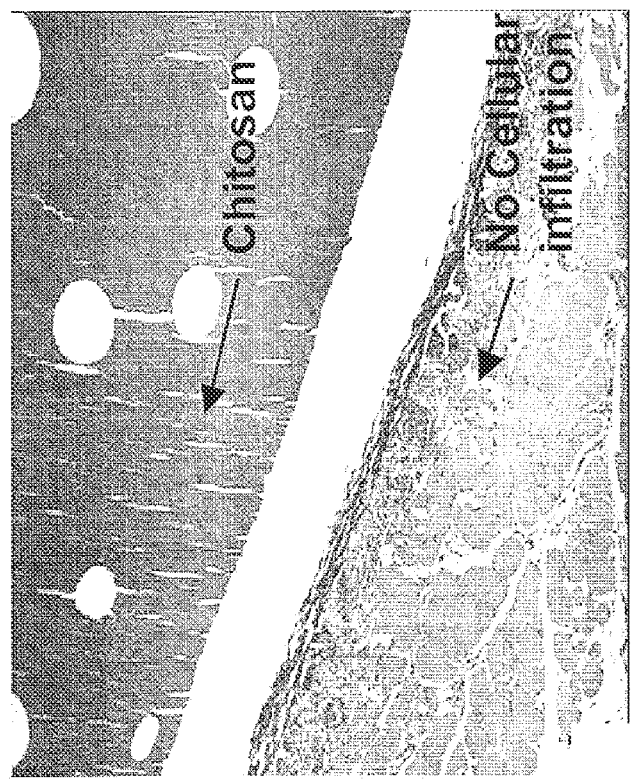

Low (5% w/w) to minimal (<1% w/w) residual acid salt content in a composition of the present invention enhanced the composition's biocompatibility by removing composition dissolution effects and cytotoxicity directly associated with the chitosan acid salt. At lower levels (<3% w/w) of chitosan acid salt in the chitosan matrix, the original structure of chitosan matrix within the composition is maintained on wetting and viable cells readily infiltrate through the matrix. FIGS. 1A and 1B show two histopathology slides (rat, seven days after subcutaneous implant) that demonstrate the effect of the presence of acid salt in test compositions on the ability of cells to infiltrate the composition.

The compositions shown in FIGS. 1A and 1B are chitosan (88% DDA no gelatin) compressed compositions. These compositions were prepared by dissolution of chitosan in aqueous acetic acid solution, pouring the aqueous chitosan acetic acid solution mixture into mold cavities; freezing and cryogenically inducing phase separation of ice and molded chitosan acetate cake; sublimation of the ice; volatilization (or not) of acetic acid from the dried cake; and thermal compression of dried cake as described previously.

In FIG. 1A, with acid present (>5% w/w) the chitosan material of the composition was globular (loss of original matrix structure) and had no cellular infiltration, but in FIG. 1B when the acid was substantially removed (<3% w/w) the chitosan matrix of the composition maintained its original lamella structure, appeared fibrillar, and shows considerable cellular infiltration. Acid was removed in the composition shown in FIG. 1B by a volatilization process to less than 3% w/w.

This experiment demonstrates that a composition acid content greater than 5% w/w would adversely affect the bioabsorption rate of chitosan materials. The results of the study demonstrate loss of original freeze-dried internal interconnected lamella structure and adverse cytotoxicity in the higher acid content chitosan matrices. This combination of loss of interconnected porous structure and cytotoxicity severely restricts the ability of cells such as neutrophils, leucocytes and monocytes to infiltrate the composition. As it is cellular infiltration and phagocytosis which are primarily responsible for biomaterial degradation processes, restricted cellular infiltration induced by water-soluble, cytotoxic chitosan acid salt adversely affects biodegradation and hence, rate of bioabsorption.

Additionally, the inventors have determined that higher weight percentages of acid salt, such as greater than 8% w/w, may induce acidotic toxicity in the case of peritoneal implantation. Accordingly, the inventors determined that reducing the presence of acid salt in implanted chitosan below 8% w/w facilitates chitosan absorption and decreases the risk of acidotic toxicity.

The inventors also determined, however, that the removal or substantial reduction of acid from the compositions reduces tissue adherence properties. These altered adherence properties based on the amount of acid present in the compositions can be used to customize the compositions for various hemostatic applications, etc., to render these compositions more or less adherent and to take into account the toxicity tolerance of a contemplated application.

Example 2

Reduced Acid Content and Cellular Infiltration in 50:50 Chitosan:Gelatin Compressed Compositions Two different approaches were pursued in an effort to achieve increased adherence efficacy of low-acid 50:50 chitosan:gelatin compressed compositions that were either foamed or not foamed.

Both approaches removed acid by the volatilization process to a level sufficient for achieving adherence (2%-5%) but also removed enough acid such that cytotoxicity or acidosis related toxicity were not major concerns.

The first approach started with a composition form having high adherence properties prior to low acid treatment with the goal of maintaining sufficient adherence properties to meet efficacy goals after low acid treatment. The second approach involved a novel low acid production process developed by the inventors to gently remove acid to minimize the effects of moisture on the composition's microstructure. This second approach used a low level of less-volatile co-acid (e.g. lactic, glycolic, malic, citric, succinic acids, etc.) which remained in the chitosan composition after the more volatile acid has been removed substantially by volatilization involving heat and humidity.

Interestingly, the reduction of acetic acid in the compositions to a low content near 3% w/w resulted in enhanced adherence of the compressed 50:50 chitosan:gelatin compositions when compared to higher acetic acid content compressed 50:50 chitosan:gelatin compositions (20% w/w).

Figure 2:
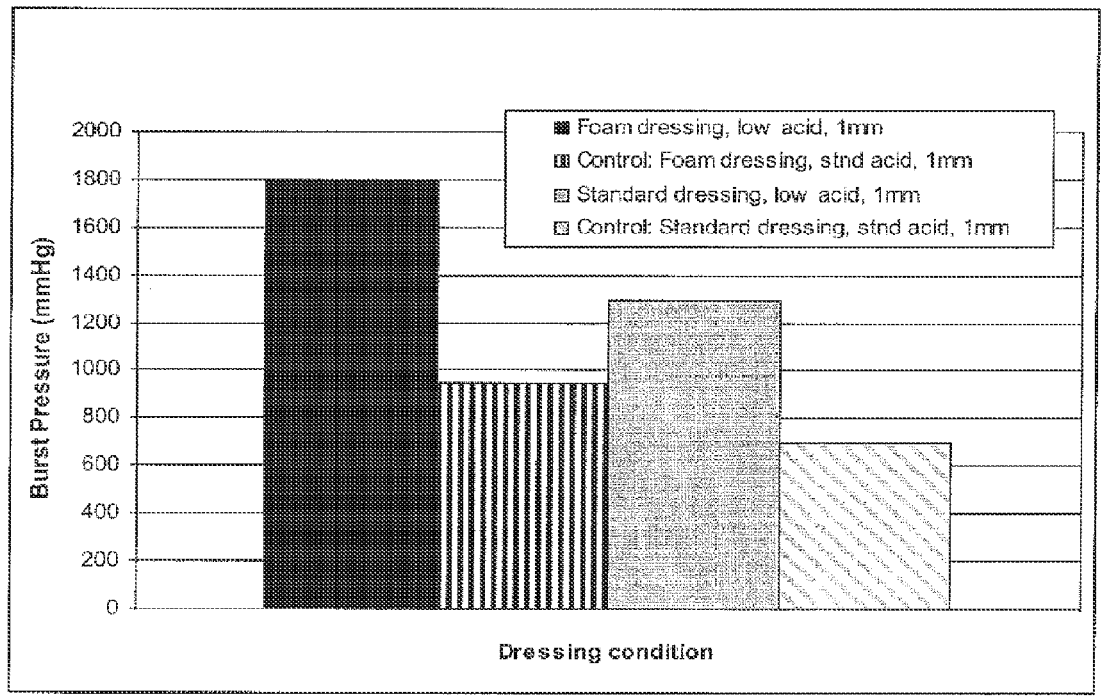
FIG. 2. Graph showing in vitro simulated arterial wound sealing (SAWS) testing results for test samples with standard acid (~20%) and low acid (~3%) content.

FIG. 2 shows the results of simulated arterial wound sealing (SAWS) for two sets of paired compressed 50:50 chitosan:gelatin compositions. SAWS provides the burst failure threshold that a standard HemCon composition can resist when attached to a standard flat PVC surface with stress applied normal to the PVC surface through a central 4 mm diameter column of bovine whole blood at room temperature under dynamic ramping conditions of 8 mmHg/s. Prior to the pressure ramp, there is a pre-attachment 10 second submersion in bovine whole blood at room temperature and an immediate subsequent three minute pressure attachment application of 55 kPa of the wetted composition to the PVC surface.

In FIG. 2, results from two identical pairs of compressed 50:50 chitosan:gelatin compositions are shown with the exception that the first pair comprises foamed chitosan:gelatin compositions and the second pair comprises chitosan:gelatin compositions that have not been foamed. The first pair of compressed 50:50 chitosan:gelatin foamed compositions showed that the low acid (~3% w/w) composition had a failure pressure of 1800 mmHg while the composition with an acid content close to 20% w/w had a failure pressure of 950 mmHg. The second pair of compressed 50:50 chitosan:gelatin non-foamed compositions showed that the low acid (~3% w/w) composition had a failure pressure of 1300 mmHg while the composition with an acid content close to 20% w/w had a failure pressure of 700 mmHg.

Thus, the inventors determined that the compressed 50:50 chitosan:gelatin foamed compositions with a low (~3% w/w) acid content demonstrated increased adherence when compared to non-foamed counterpart compositions.

Example 3

Figure 3:
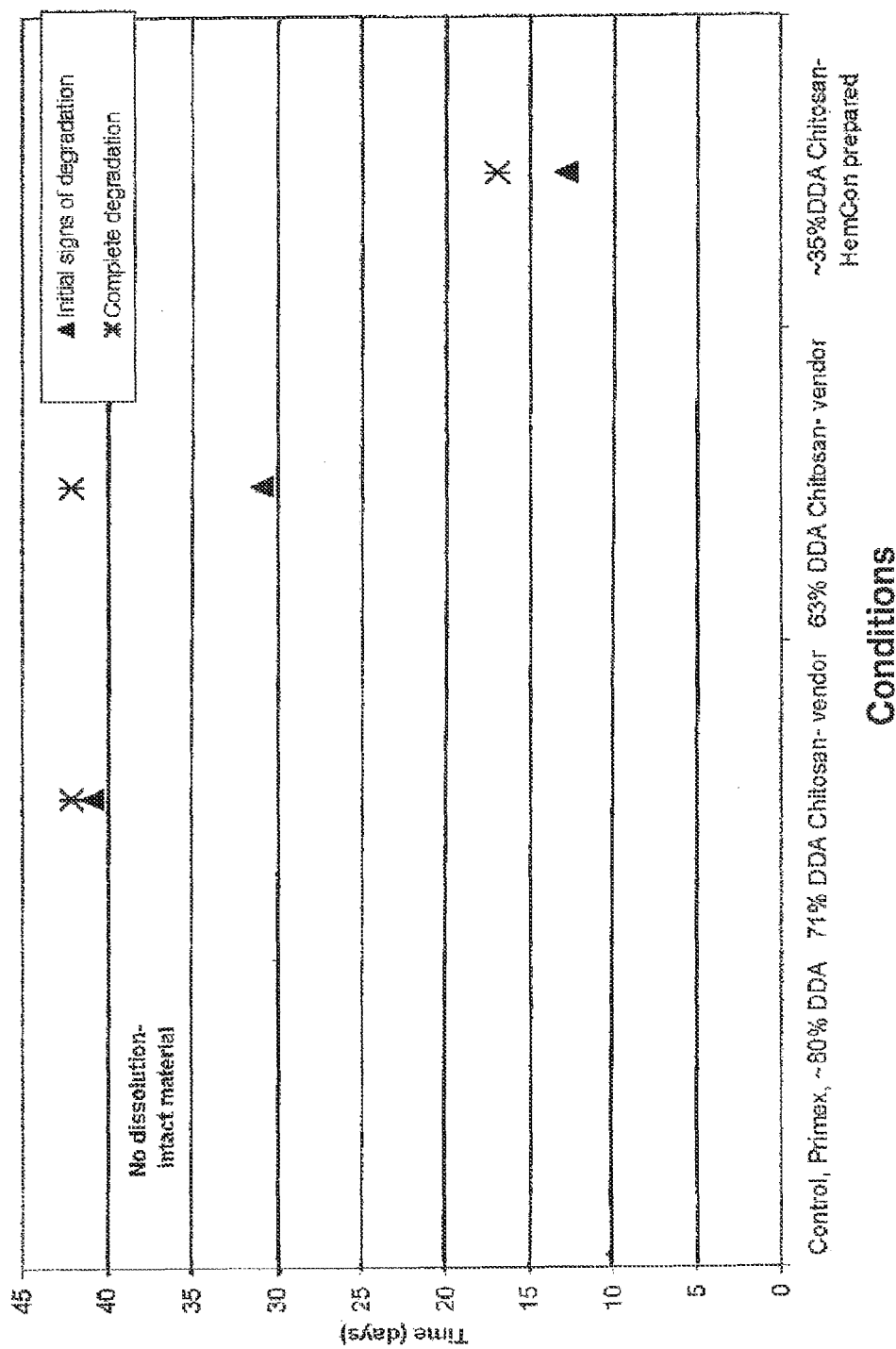
FIG. 3. Graph showing lysozyme susceptibility of compositions comprising chitosan having different DDA levels.
Figure 4A:
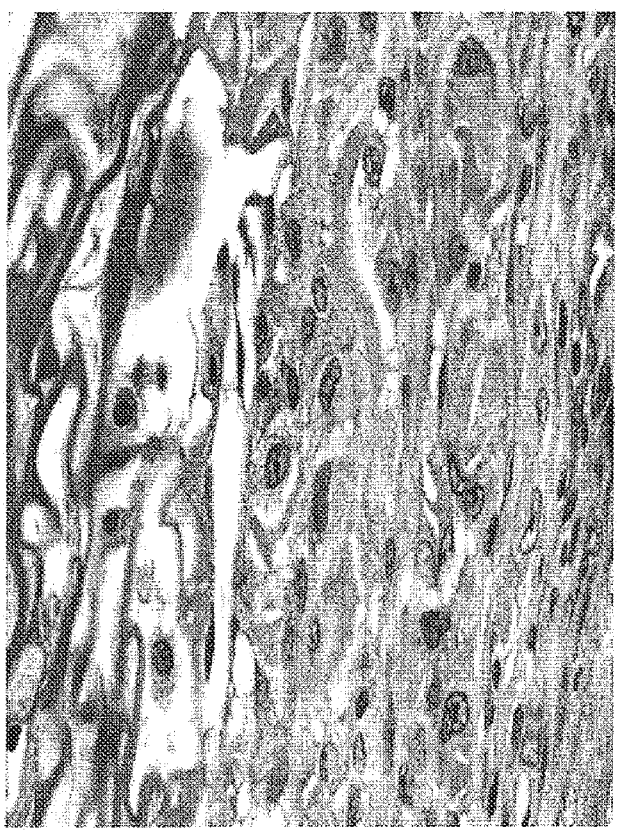
FIGS. 4A and 4B. Slides showing histopathology of an explanted test composition comprising chitosan having a ~35% DDA after 8 days at 20× magnification (FIG. 4A) and at 60× magnification (FIG. 4B), respectively (rat, intraperitoneal).
Figure 4B:
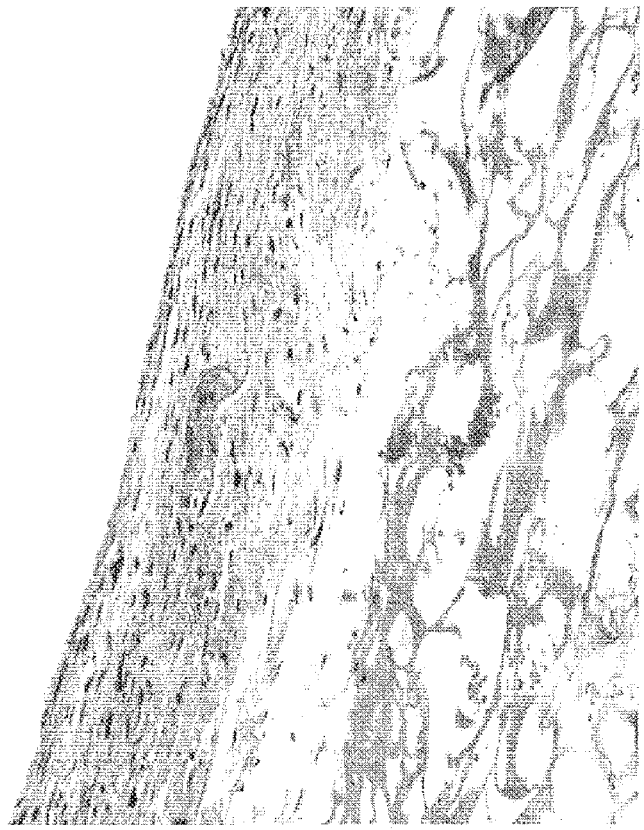
Figure 5A:
FIGS. 5A and 5B. Slides showing histopathology of an explanted test composition comprising chitosan having a ~35% DDA after 28 days at 20× magnification (FIG. 5A) and at 60× magnification (FIG. 5B), respectively (rat, intraperitoneal).
Figure 5B:
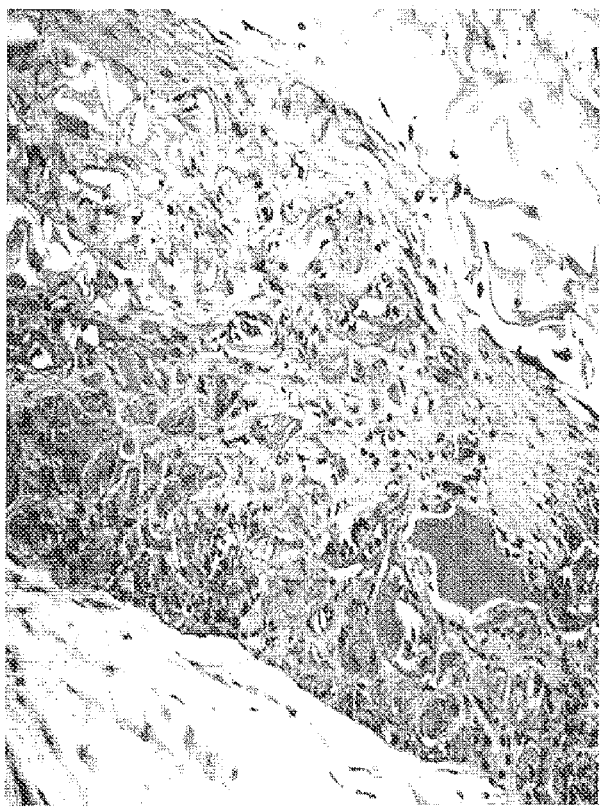

Comparative In Vitro Bioabsorption Testing of 50:50 Chitosan:Gelatin Foamed and Compressed Compositions Comprising Chitosan of Varying Degrees of Deacetylation 50:50 chitosan:gelatin foamed and compressed compositions, only different in degree of deacetylation (DDA), were tested in lysozyme at 37° C. for time-dependent susceptibility to absorption. As shown in FIG. 3, the compositions became increasingly susceptible to time dependent absorption in lysozyme as the DDA decreased. The compositions were prepared using the same procedures. The compositions were processed with Primex chitosan (DDA ≥80%), non-acetylated ultrapure FMC Novamatrix chitosan (DDA ≥85%) and acetylated ultrapure FMC Novamatrix chitosans. Varying degrees of deacetylation, 71%, 63%, and 35% were obtained for the test compositions.

The test compositions were suspended in a 0.37% w/w lysozyme solution at 37° C. Visual inspection of the samples was made at regular intervals. Visual inspection was made daily during normal working day (8:00 am to 5:00 pm) with at least one inspection at the beginning of the day and one at the end. The time of first appearance of degradation by appearance of sample fragmentation in the sample aqueous lysozyme suspensions was recorded as the initial time of degradation. The time that suspended sample fragments no longer could be observed in the test mixture was recorded as time to 100% degradation.

Example 4

Rat, Intraperitoneal Bioabsorption Comparative Study of Various Compositions

A rat intraperitoneal absorption study was performed to determine absorbability and biocompatibility of various compositions comprising chitosan having a degree of deacetylation varying from 88% deacetylated through to fully reacetylated chitosan (0% DDA).
a. Test Composition Components and Preparation
FIGS. 9A and 9B provide a Master Table of all sample and control compositions, treatments, dimensions, compressions and densities used in Examples 4 to 8. Samples A, B, C, E, F, G, H, I, J, K and M and controls AC and AD were used in the rat implant study of Example 4.

Deacetylated chitosans having an 88% DDA and a 63% DDA were obtained as ultrapure grade chitosan from FMC Novamatrix in Norway. The materials were off-white powders, with less than 0.5% insolubles, less than 1% ash content, less than 0.3% protein content, less than 10 pm heavy metals, and less than 10 cfu/g bioburden. The molecular weight for the chitosans was greater than 60 kDa for the number average. Endotoxin analysis was performed on the materials received and demonstrated endotoxin EU was less than 10 EU/g. Water used in these studies was water for injection. Acetic acid was obtained from Emprove at 100% purity. The gelatin (porcine source) was obtained from Gelita and contained endotoxin less than 90 EU/g. The gelatin had a 286 g bloom, 5.54 pH, 0.01% ash content, and less than 100 cfu/g bioburden. The microdispersed oxidized cellulose (Na/Ca salt of polyanhydroglucuronic acid) was obtained from Synthesia A.S. (Czech Republic) as a biomedical grade material. The crosslinking agent 1-Ethyl-3-[3-dimethylaminopropyl]carbodiimide hydrochloride (EDC) was obtained from Pierce, Cat no 22980. Acetic anhydride was of ACS reagent grade obtained from JT Baker. Infrared analyses of the final reacetylated chitosan demonstrated that there was no residual 0-acetyl ester functionality (absorbance 1850 $cm^{-1}$).

All preparation of compositions was performed in a controlled environment that was monitored for environmental bioburden. The compositions were prepared from freezing and freeze-drying 2% w/w aqueous solution of chitosan in 2% w/w aqueous acetic solutions or 1% w/w gelatin and 1% w/w chitosan aqueous solutions in 2% acetic acid aqueous solution. Test implant samples B, C, E, F, G, H, I, J, K, and M were close to 14 mg in mass while implant sample A with EDC cross-linking was 5 mg in mass. In the case of gelatin chitosan composition (Sample A), EDC was added to a carbonic acid, acidified aqueous mixture (in the absence of other acid) to crosslink the matrix. Also another composition (Sample I) included microdispersed oxidized cellulose (mdoc) in combination with chitosan. Two of the compositions were prepared from chitosan that had been reacetylated from 88% degree of deacetylation by application of acetic anhydride (Samples K and M). After freeze drying, the compositions with moisture content at or below 5% w/w moisture were thermally compressed at 80±1° C. from close to 7 to 8 mm thickness to either 2 mm or 1 mm thickness (only Sample A was prepared at 2 mm thickness).

The eleven test compositions were investigated with controls of oxidized cellulose matrix (Surgicel™) and sham surgery. The test compositions comprised chitosan having degrees of deacetylation of about 88%, 71%, 63%, 35% (reacetylated) and 0% (reacetylated).
b. Test Subjects
Rats (Rat, Sprague Dawley, male, 120-200 g, N=6 per condition and time point except sham where N=4) were anaesthetized, a sterile surgical field was prepared and a ventral incision was made to access the intraperitoneal cavity. A test composition piece (5 mm×10 mm×1 mm, 14 mg) was attached by placement and holding over a laceration injury to the liver for 2 minutes resulting in cessation of bleeding, and the surgical site was closed. Generally chitosan was well adhered to the liver after being held for 2 minutes while the control Surgicel™ being non-adhesive only stayed in placed through clotting of blood around and through its non-woven structure. Animals were returned to their cages to recover from the anesthesia. Animals were provided water and food and monitored for sign of loss of appetite or lethargy. Animals were sacrificed by administration of a lethal dose of barbiturate. Test samples were blinded to surgical personnel and pathology until after completion of the pathology report.

Initially explant times were designed to be 49 days and 97 days, however this was changed to the shorter times of 7 and 28 days when unexpected dermal lesions were exhibited early in the study. Blood specimens, target organs, dermal lesion biopsies (if present), and explanted test composition (if present) were collected from each test subject. All blood samples were tested at time zero and at time of explant. At the time of explant, subjects were inspected for general health and the intraperitoneal cavity was visually inspected for the test composition, test composition fragments, organ health, healing of the injured liver lobe, and surgical adhesions. Any fragmentation of the test composition was considered undesirable. The incidence of fragmentation and of dermal lesions in the different test sample forms are listed in FIG. 10.

The dermal lesions (FIG. 10) were clearly visible on exposed skin around the animal ears, nose, mouth, feet and tail. Once the subjects were un-blinded, the lesions were found to be present only in the test subjects of groups with 63% DDA chitosan. The lesions appeared approximately three to four days post-implantation of the test composition on an injured liver in the rat intraperitoneal space. The dermal lesions resolved after close to ten days following implantation. The bioabsorption study was terminated early to allow determination of possible causes of the dermal lesions. The conditions of sample preparation, the blinding of the study, the handling of the samples and the low residual acidity were sufficiently well controlled to eliminate possibilities of contamination events and surgical procedural problems. The consistent appearance of the lesions in only the 63% DDA chitosan groups suggested a material inflammatory/toxicity problem.

The material compositions in which lesions were observed contained rapidly absorbing chitosan with a degree of deacetylation of 63% with unreacted C2 amine functionality (i.e., not crosslinked or reacted with an electrophilic species, etc.).

Figure 6A:
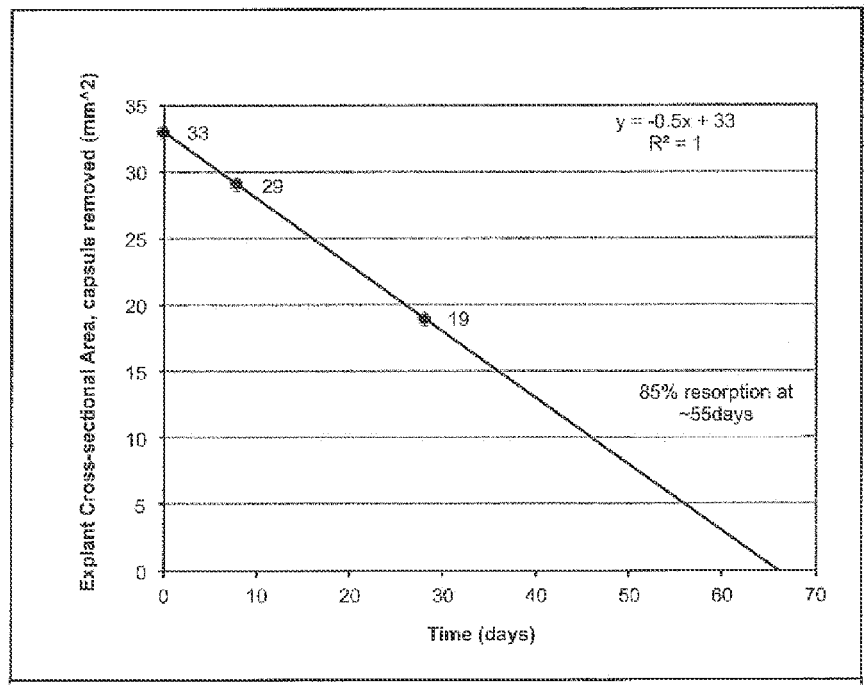
FIGS. 6A and 6B. Graphs showing extrapolated absorption times for compositions comprising chitosan at 0% DDA (A) and ~35% (B) DDA.
Figure 6B:
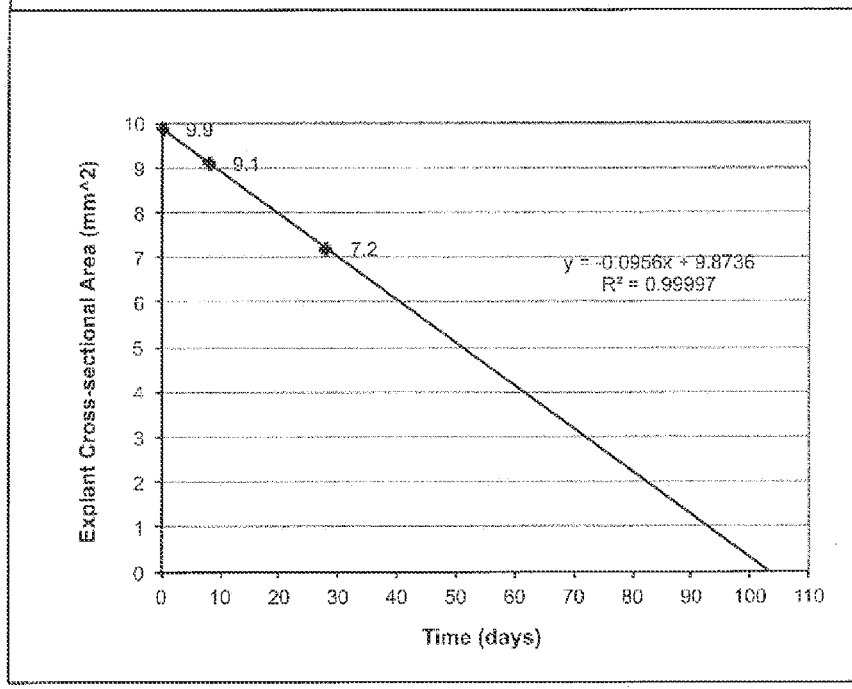

In terms of bioabsorption, absence of dermal lesions, absence of in vivo fragmentation, ability to control bleeding (not accounted for in FIG. 10) and excellent histopathology, the top performing sample was the 50:50 chitosan:gelatin foamed and compressed composition (Sample K) prepared by reacetylation of chitosan from 88% DDA to ~35% DDA chitosan. This composition did not give rise to dermal lesions or fragmentation and demonstrated substantial but incomplete absorption within 28 days after implantation. FIGS. 4A and 4B and 5A and 5B demonstrate desirable active cellular infiltration into the 50:50 chitosan:gelatin foamed and compressed composition Sample K at 8 and 28 days, respectively. FIGS. 6A and 6B predict the time to complete absorption (to at least 85% absorbed) of test compositions Samples M and K respectively within 90 days based upon measurement of the explanted material test composition histological cross-sectional area at 0, 8, and 28 days after implantation.

Example 5

Cytokine Elevation on Bioabsorption

To identify the source of the dermal lesions observed in the rat absorption model as discussed above in Example 4, a number of cytokine possibilities were considered. Cytokine IL-1β was chosen for investigation because it is a member of the interleukin 1 cytokine family. This cytokine is produced by activated macrophages as a proprotein, which is proteolytically processed to its active form by caspase 1 (CASP1/ICE). This cytokine is an important mediator of the inflammatory response, and is involved in a variety of cellular activities, including cell proliferation, differentiation, and apoptosis.

A study for elevation in IL-1β was conducted ex vivo using blood sera collected from the rat test subjects from Example 4 that demonstrated lesions, as well as, the control test subjects and the test subjects that did not demonstrate lesions. It was hypothesized that if the test composition was activating macrophages that are, in turn, producing IL-1β this may explain the lesions that present similar to atopic dermatitis. It was also hypothesized that the macrophage activation and subsequent cytokine elevation are dependent upon the active breakdown of chitosan material to its biodegradation products during the bioabsorption process.

Figure 7:
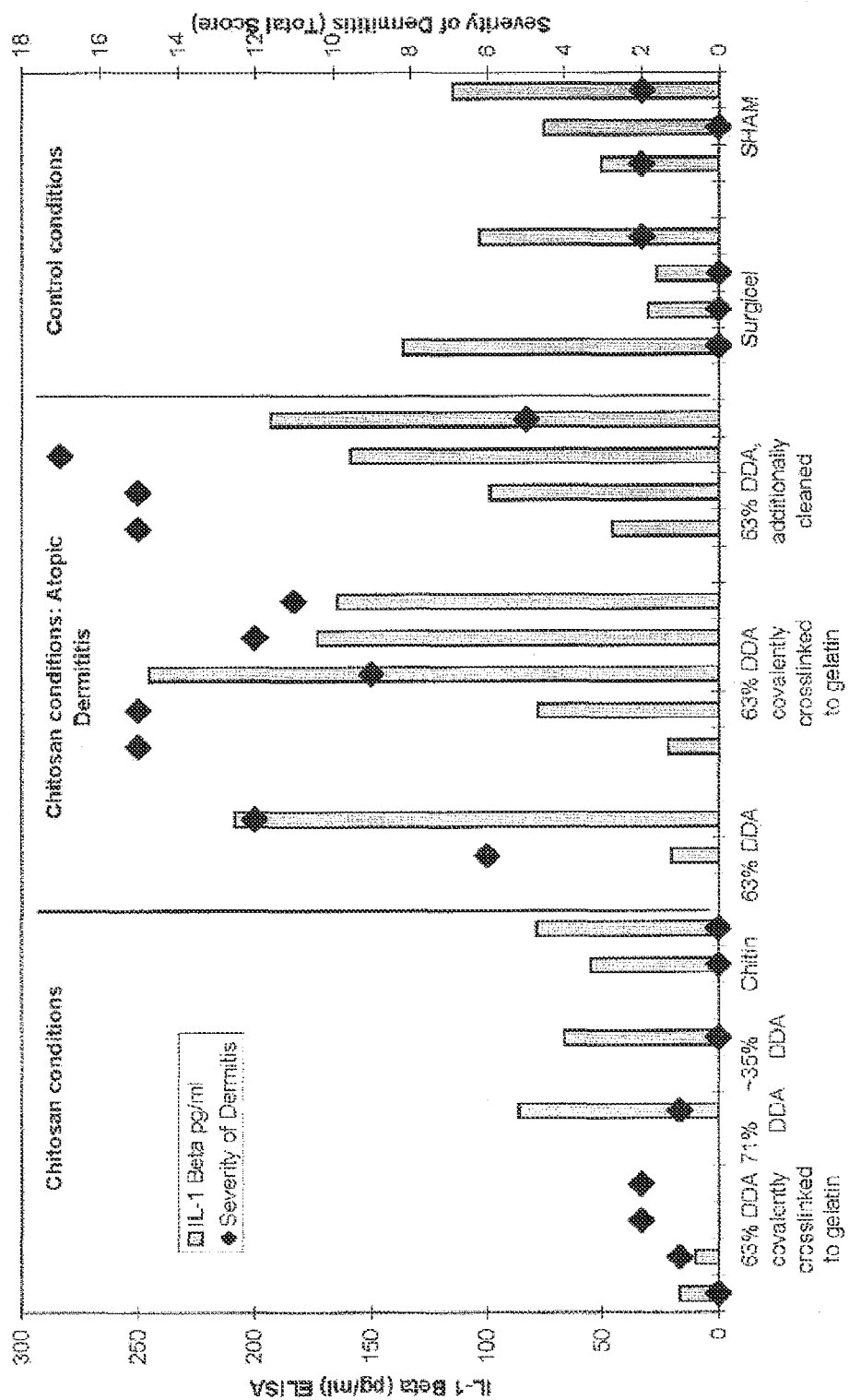
FIG. 7. Graph showing the total dermatitis score for individual rats and corresponding rat sera IL-1β [pg/ml].

The blood sera were tested using a standard ELISA (RandD Systems, Quantikine Rat IL-1/IL-1F2 Immunoassay, Cat No. RLB00). The sera samples from the rats of Example 4 seven days after implantation were tested. The results of the blood sera testing demonstrated that rats with lesions exhibited a statistically significant ($P<0.01$) elevation of IL-1β compared to rats with no lesions (see FIG. 7). The total lesion scale of 0-18 in FIG. 7 was based on the sum of a lesion ranking index (see FIGS. 8A, 8B, 8C, and 8D) of 0-4 being summed over the results from 6 animals. The lesion scoring scale assigns lesion scores as follows: zero for no observed lesions; one for mild to red or crust; two for moderate to red with crusts; three for moderate or severe to ulceration; and four for severe to sloughing and necrosis.

FIG. 8A shows rat 90-14A with a tail lesion sated at three. FIG. 8B shows an example of eyes rated at three and ears rated at two. FIG. 8C shows a rat's nose and mouth rated at three. FIG. 8D shows a rat's nose and mouth rated at a three. Consistent with this finding, the compositions comprising crosslinked chitosan did not exhibit elevated IL-1β and the compositions comprising chitosan with DDA greater than 70% and less than 40% did not demonstrate elevated IL-1β while compositions comprising chitosan materials with degree of deacetylation greater than 35% but less than 70%, such as 63%, demonstrated elevated IL-1β as well as atopic dermatitis.

The inventors found that the occurrence of dermal lesions is material mediated and that the absorption process induces changes in the chitosan which mediates cytokine elevation. The inventors of the present invention also surprisingly and unexpectedly discovered that compositions comprising chitosan reacetylated below 40% DDA and, specifically, compositions comprising chitosan reacetylated to about 35% DDA bioabsorbs rapidly without causing up-regulation of IL-1β cytokine.

Example 6

A Rapid Screening Test for Bioabsorbable Chitosan Biocompatibility

It is evident that the intraperitoneal implantation of compositions comprising non-crosslinked 63% DDA chitosan resulted in dermal lesions in rats. Whether the 63% degree of deacetylation (DDA) chitosan was produced by directed deacetylation from chitin, or reacetylation from a high purity 88% DDA chitosan, compositions comprising either 65% DDA bioabsorbing chitosan produced elevated IL-1β and atopic dermatitis. The IL-1β testing results of the rat sera supports the understanding that the degradation process or degradation products from compositions comprising chitosan having about a 63% DDA activate the undesirable macrophage production of IL-1β in the blood.

Standard biocompatibility testing for a rapidly bioabsorbable implant material (limited implant contact duration) performed according to the International Organization for Standardization (Biological evaluation of medical devices—Pt 1 ISO 10993-1) suggests that chitosan having a 63% DDA has acceptable biocompatibility for implantation. The standard ISO 10993-1 testing performed included tests for cytotoxicity, irritation, and acute systemic toxicity.

Importantly, however, because ISO 10993-1 standard testing was not predictive of the dermal lesions observed during bioabsorption, the present inventors developed a modified Acute Systemic Toxicity (AST) test referred to as Mouse Lesion Test (MLT). Additionally, the inventors developed the MLT to provide a reliable test that does not require surgical implantation to screen for biocompatible bioabsorbable chitosan. This is because surgical implantation studies require highly skilled personnel, special surgical facilities, and animal use approvals, and can consume significant development resources.

The MLT test method was described previously in part C of this invention disclosure. The MLT is a modification of the standard ISO 10993-1 Acute Systemic Test in mice. The differences between the MLT and AST in the testing methodology are the following: (1) the MLT utilizes a higher concentration of test composition than is specified for the standard AST; (2) the MLT test window is extended to 7-days from 3-days; (3) there are additional observational acceptance/failure criteria for the testing lab other than weight loss and/or death; and (4) the test chitosan material is aseptically pre-degraded using lysozyme to prime the system with biodegradation products. The MLT is a low cost test that can be used as a standard test in contracting testing laboratories to quickly and effectively screen preparations of bioabsorbing poly-β-(1-4)-N-acetyl-D-glucosamine (both chitin and chitosan) for undesirable IL-1β elevation associated with biodegradation product formation. As well as the standard toxicity acceptance/failure responses of weight loss and/or death that are used in the AST test, the MLT includes pilo-erection, lethargy, hair loss, and lesion appearance as these are all manifestations of an elevated cytokine response. The dosing regime in the MLT developed of 2,000 mg/kg (40 mg/20 g mouse) is consistent with bioabsorption guidelines ASTM F2150-07, ASTM F1983 and ISO 10993-9 and provides clear indication of presence or absence of the acute IL-1β response associated with bioabsorption of some chitosans.

Samples from the rat absorption study, including Sample C and Sample K from Example 4, were tested using the MLT test (N=5). Sample C in which lesions were observed (compressed compositions with <5% acid w/w content comprising wherein the 63% DDA chitosan was prepared using direct deacetylation) and Sample K in which no lesions were observed (compressed compositions with <5% acid w/w content comprising 50:50 chitosan:gelatin foamed wherein the chitosan was prepared using 88% DDA chitosan reacetylated to about 35% DDA) were tested.

Discrimination was seen between test results for Sample C and Sample K in mice. For test samples with Sample C pre-degraded with lysozyme, on day 4, all test mice scored 0 for lesions; however the laboratory technician noted that the animals' coats were rough in appearance. The animals were bright, alert, and responsive. On day 5, all of the test mice scored 1 (mild) for lesions. On day 6, all the test mice scored 2 (moderate) for lesions. They were noted to have red, thickened, crusty skin all over their bodies. Their eyes were squinted and surrounding tissue appeared pink and swollen. They also appeared slightly dehydrated. The water bottle was checked and was functional. The animals' hair was noted to be patchy, especially on the abdomen. For test samples with Sample K pre-degraded with lysozyme, no lesions appeared on test or control mice. All of the mice appeared normal and remained healthy thru to study conclusion (day 7).

Samples O, P, Q, R, S, T, U, and V comprised the same starting ultrapure 88% DDA chitosan that was reacetylated to a final DDA with the only difference between these samples (other than the controls that were not pre-degraded with lysozyme) being extent of chitosan reacetylation from aqueous acetic anhydride. All samples O, P, Q, R, S, T, U, and V were compressed compositions with <5% acid w/w content comprising 50:50 chitosan:gelatin foamed wherein the chitosan was prepared using 88% DDA chitosan reacetylated to the desired DDA.

Sample D was prepared using a compressed composition with <5% acid w/w content comprising 63% DDA chitosan prepared using direct deacetylation.

The composition of sample reference number N was prepared using UP FMC chitosan of 88% DDA as indicated in FIG. 9.

Sample AB was prepared from food grade glucosamine and was intended as a control for the monomer of poly-β-(1-4)-N-glucosamine All samples in FIG. 10 were tested at 40 mg/ml. Injection of 1 ml of the sample pre-degraded extract was injected into the intraperitoneal cavity of a 20 g mouse to provide a 2,000 mg/kg dose. All testing was conducted for a 7-day testing period with signs of toxicity being presented on day 4 with highest levels being presented by day 7 with survival of the animal. The results of this MLT testing are provided in FIG. 11.

As shown in FIG. 11, the MLT test demonstrated that compositions comprising chitosan having a 35% DDA, or lower than 30% DDA, produced no clinical toxicity signs, such as pilo-erection, lethargy, weight loss, hair loss, lesion, and death. By contrast, compositions comprising chitosan having a 45%, 60%, and 63% DDA produced clinical toxicity signs, including one or more of pilo-erection, lethargy, weight loss, hair loss, lesion, and death. Accordingly, this test assisted identification of the biocompatible DDA range chitosan of falling below 45% DDA and encompassing 35% DDA and less than 30% DDA.

Example 7

Efficacy

Prototype chitosan hemostatic test compositions W, X, Y, and Z with controls AE and AC were evaluated for hemostatic efficacy in swine models of moderate and robust hemorrhagic bleeding.

The compressed compositions W, X, Y, and Z comprising 50:50 gelatin:chitosan solutions described (see FIG. 9) used chitosan prepared with ultrapure 88% DDA chitosan that was reacetylated to a desired DDA and also involving foaming the solution prior to freezing and freeze drying as described in Example 4. The solutions were foamed because the inventors found that foamed compositions enabled significant improvement in composition flexibility and tissue compliance which eased application of the compositions as well as enhanced hemostatic efficacy. Foaming of the 50:50 chitosan:gelatin solutions to near 0.6 g/cm³ density was achieved by whisking the mixture to introduce aeration.

As shown in FIG. 12, the test compositions also employed different low acid contents ranging between about 2.7% w/w to about 5% w/w.

The test compositions were evaluated for hemostatic efficacy in both difficult to control oozing surgical bleeding and high pressure high volume traumatic injury-type bleeding.

Healthy swine of weight 80 lbs to 130 lbs were anaesthetized, a laparotomy was made to expose the abdominal cavity. Exposure was performed in a manner to avoid trauma to vascular, urinary, bilious, and lymphatic structures.

Swine parenchymal models of acute heparinized bleeding following either liver capsular stripping or spleen capsular stripping were employed as both these models of parenchymal bleeding are typical of difficult to control oozing surgical bleeding. A total of 17 swine were tested for either or both of heparinized liver capsular stripping and spleen stripping.

For animals where both liver capsular stripping and spleen stripping, injuries were used: one wound was created on each of two liver lobes (left medial and left lateral) and one wound on spleen. An infusion of heparin (10,000 u) was applied to maintain an activated clotting times (ACT) greater than 250 seconds. ACT was tested every 15 minutes and additional heparin (10,000 u) was administered to maintain the ACT >250 seconds. Hemostatic testing was performed with capsular stripping injuries of 2 cm×2 cm×0.3 cm on the spleen and on the liver. Test and control compositions were cut such that a 2 cm×2 cm piece would be inserted within the injury and a 5 cm×5 cm piece was placed over this and over the injury. A successful test on the liver or the spleen was one that after holding uniform pressure over the applied compositions with 4"×4", 48-ply surgical gauze for three minutes there was no subsequent bleeding and there was no bleeding within 20 minutes of removal of pressure.

A total of 3 swine were tested using a swine aorta perforation model, which is a good model of severe hemorrhagic bleeding. These swine were not heparinized. The abdominal aorta was exposed with placement of a ~25 cm diameter circular retractor inside the abdominal cavity immediately over the aorta. The injury to the aorta was made using a 3 mm scalpel incision through the aorta and removal of a contiguous 4 mm diameter section of the aorta using a 4 mm diameter vascular punch. Mean arterial pressure (MAP) was maintained near 60 mmHg using Hextend™ infusion. Test and control compositions were 5 cm×5 cm. An injury could be used up to 6 times in an animal with MAP maintained at or near 60 mmHg and with removal of a previous dressing and swabbing of the immediate wound area with clean gauze wetted with saline to remove any chitosan residue. A successful test on the aorta was one, that after holding uniform pressure over the applied composition with 4"×4", 48 ply surgical gauze for three minutes, there was no immediate bleeding and there was no bleeding within 30 minutes of removal of pressure.

During surgery it was observed that the low acid content compositions while generally less adherent to the tissue than compositions with higher acid contents, had increased resistance to dissolution and still exhibited very good efficacy. Also, the decreased adherence of the low acid content compositions beneficially resulted in minimal tissue damage upon removal and eased residue clean up.

The test results in FIG. 12 show that the compositions comprising chitosan having a DDA of 35% were effective in 67% of swine tested in the heparinized liver capsular stripping model. The test results also show that the compositions comprising chitosan having a DDA of less than or equal to 30% were effective in 63% of swine tested in the heparinized liver capsular stripping model, 80% of swine tested in the heparinized spleen capsular stripping model, and 100% of swine tested in the swine aorta perforation model.

Example 8

Bioabsorption, Biocompatibility and Hemostasis of 35% DDA Chitosan

Compressed compositions comprising 50:50 gelatin:chitosan foamed solutions using chitosan prepared with ultrapure 88% DDA chitosan that was reacetylated to a 20% DDA and having an acid content close to or less than 5% were prepared as described in Example 4.

FIG. 13 shows the results of testing these compositions in 28-day rat intraperitoneal absorption, biocompatibility (MEM elution, AST, MLT, irritation) and swine hemostatic testing as described above in Example 7 relative to a commercial hemostatic absorbable control composition, Surgicel™, composed of oxidized cellulose.

The tested composition which is about 30% bioabsorbed after 28 days of implantation, demonstrates good cytotoxicity, good acute systemic toxicity, acceptable low irritation score, and effective hemostatic control in bleeding situations that are either difficult to control surgical-type bleeding or heavy pressure and heavy flow traumatic injury-type bleeding. The tested composition meets all the requirements of an absorbable composition and is shown to be superior to the commercial control in terms of hemostatic efficacy.

The invention claimed is:

1. A biocompatible, bioabsorbable deacetylated and reacetylated chitosan composition comprising a reacetylated chitosan having a molecular weight of about 90 kDa to about 170 kDa and a degree of N-deacetylation of between about 15% and 40%.

2. The composition of claim 1, wherein the composition is initially soluble in an aqueous solution below or at about pH 6.5.

3. The composition of claim 1, further comprising at least one of an acid content between about 0% (w/w) and 8% (w/w) and an active ingredient selected from the group consisting of calcium, albumin, fibrinogen, thrombin, factor VIIa, factor XIII, thromboxane A2, prostaglandin-2a, activated Protein C, vitronectin, chondroitin sulfate, heparan sulfate, keratan sulfate, glucosamine, heparin, decorin, biglycan, testican, fibromodulin, lumican, versican, neurocan, aggrecan, perlecan, lysozyme, lysly oxidase, hexose oxidase, cholesterol oxidase, pyranose oxidase, choline oxidase, pyruvate oxidase, glycollate oxidase and/or aminoacid oxidase, hexose, cholesterol, pyranose, choline, pyruvate, glycollate, aminoacid, epidermal growth factor, platelet derived growth factor, Von Willebrand factor, tumor necrosis factor (TNF), transforming growth factor (TGF), insulin like growth factor, fibroblast growth factor (FGF), keratinocyte growth factor, vascular endothelial growth factor (VEGF), nerve growth factor, bone morphogenic protein (BMP), hepatoma derived growth factor (HDGF), interleukin, amphiregulin, retinoic acid, erythropoietin, mafenide acetate, silver sulfadiazine, silver nitrate, nanocrystalline silver, penicillin, ampicillin, methicillin, amoxicillin, clavamox, clavulanic acid, aztreonam, imipenem, streptomycin, kanamycin, tobramycin, gentamicin, vancomycin, clindamycin, lincomycin, erythromycin, polymyxin, bacitracin, amphotericin, nystatin, rifampicin, tetracycline, doxycycline, chloramphenicol, cefuroxime, cefradine, flucloxacillin, floxacillin, dicloxacillin, potassium clavulanate, clotrimazole, cyclopiroxalomine, terbidifine, ketoconazole, paclitaxel, docetaxel, imatinib, exemestane, tamoxifen, vemurafenib, ipilimumab, dacarbazine, interleukin-2, abiraterone, doxorubicin, 5-fluorouracil, tamoxifen, octreotide, sorafenib, resveratrol, ketamine, diclofenac, ibuprofen, paracetamol, codeine, oxycodone, hydrocodone, dihydromorphine, pethidine, buprenorphine, tramadol, venlafaxine, flupirtine, carbamazepine, gabapentin, pregabalin, lidocaine, autologous cell lines, stem cells, and combinations thereof.

4. The composition of claim 1, wherein the composition is cross-linked with at least one of gelatin and collagen.

5. The composition of claim 1, wherein the composition is capable of in vivo bioabsorption in less than one of about 90 days, about 60 days, about 30 days, and about 14 days.

6. The composition of claim 5, wherein the composition is at least 85% absorbed.

7. The composition of claim 1, wherein the composition has a degree of N-deacetylation between about 15% to 35%.

8. The composition of claim 1, wherein the composition comprises one of a freeze-dried sponge, a freeze-dried foam, a non-freeze-dried foam, an implant, a tissue scaffold, an implant device surface coating, a matrix, a fiber, a powder, a sheet, a film, a membrane, a nanofiber, a nanoparticle, and a hydrogel.

9. A method of making a biocompatible, bioabsorbable chitosan composition comprising:
obtaining deacetylated chitosan;
producing reacetylated chitosan from the deacetylated chitosan having a degree of N-deacetylation of between 15% and 30%; and
resolubilizing the reacetylated chitosan to aqueous solution using carbonic acid.

10. The method of claim 9, further comprising selecting a deacetylated chitosan starting material having at least one of a degree of N-deacetylation of between about 75% to 100% and a purity of at least 99%.

11. The method of claim 9, further comprising reducing chitosan free amine functionality of a glucosamine C-2 nitrogen of the deacetylated chitosan with an electrophile.

12. The method of claim 9, further comprising combining the resolubilized reacetylated chitosan aqueous acidic solution and an aqueous gelatin solution.

13. The method of claim 9, further comprising cross-linking the chitosan with at least one of gelatin and collagen.

14. The method of claim 13, further comprising using 1-ethyl-3-[3-dimethylaminopropyl]carbodiimide hydrochloride to accomplish the cross-linking.

15. The method of claim 9, further comprising processing the chitosan into at least one of a freeze-dried sponge, a freeze-dried foam, a non-freeze-dried foam, an implant, a tissue scaffold, an implant device surface coating, a matrix, a fiber, a powder, a sheet, a film, a membrane, a nanofiber, a nanoparticle, and a hydrogel.

16. The composition of claim 1, wherein the composition has a degree of N-deacetylation between about 20% to 35%.

17. The composition of claim 1, wherein the composition has a degree of N-deacetylation between about 20% to 30%.

18. A biocompatible, bioabsorbable deacetylated and reacetylated chitosan composition comprising a reacetylated chitosan having a degree of N-deacetylation of between 15% and 30% and cross-linked with at least one of gelatin and collagen.

19. The composition of claim 1, further comprising an acid content between about 2% (w/w) and 8% (w/w).

20. The composition of claim 18, further comprising an acid content between about 2% (w/w) and 8% (w/w).

* * * * *